US008778876B2

(12) United States Patent
Watowich et al.

(10) Patent No.: US 8,778,876 B2
(45) Date of Patent: Jul. 15, 2014

(54) SMALL-MOLECULE INHIBITORS OF DENGUE AND WEST NILE VIRUS PROTEASES

(75) Inventors: Stanley J. Watowich, Houston, TX (US); Suzanne M. Tomlinson, Galveston, TX (US); Scott Gilbertson, Pearland, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/412,448

(22) Filed: Mar. 5, 2012

(65) Prior Publication Data

US 2013/0035284 A1 Feb. 7, 2013

Related U.S. Application Data

(60) Provisional application No. 61/449,492, filed on Mar. 4, 2011.

(51) Int. Cl.

| | |
|---|---|
| ***A01N 37/18*** | (2006.01) |
| ***A61K 38/00*** | (2006.01) |
| ***A61P 31/12*** | (2006.01) |
| ***A61K 31/33*** | (2006.01) |
| *A61K 9/48* | (2006.01) |

(52) U.S. Cl.

CPC ............... *A61K 31/33* (2013.01); *A61K 9/4858* (2013.01)

USPC ........................................................... 514/3.7

(58) Field of Classification Search

CPC ............................. A61K 31/33; A61K 9/4858

See application file for complete search history.

(56) References Cited

PUBLICATIONS

Wang et al., J. Agric. Food Chem. 2007, 55, 3869-3876.*
Alvarez, 2006, Am J Trop Med Hyg 75:1113-7.
Cahour et al., 1992, J Virol 66:1535-1542.
Chanprapaph et al., 2005, Biochem Biophys Res Commun 330:1237-46.
Erbel et al., 2006, Nat Struct Mol Biol 13, 372-373.
Falgout et al., 1991, J Virol. 65:2467-2475.
Ganesh et al., 2005, Bioorg Med Chem 13, 257-264.
Gen Bank accession No. NP_041724.
Halstead, 2003, Adv Virus Res 60:421-67.
Hayden et al., 2003, Antimicrob Agents Chemother 47, 3907-3916.
Hrobowski et al., 2005, Virol J 2, 49.
Hsu et al., 2006, Curr Pharm Des 12, 1301-1314.
Lamarre et al., 2003, Nature 426, 186-189.
Latour et al., 2010, Antiviral Res 87, 213-222.
Leung et al., 2001, J Biol Chem 276, 45762-45771.
Li et al., 2005, J Biol Chem 280, 28766-28774.
Marks et al., 2001, J Med Chem 44, 2178-2187.
McDonnell and Russell, 1999, Clin Microbiol Rev 12:147-79.
Modis et al., 2003, Proc Natl Acad Sci U S A 100, 6986-6991.
Mogi and Kita, 2009, Cell Mol Life Sci 66:3821-6.
Molinari et al., 2009, J Hazard Mater 165:1074-82.
Mueller et al., 2007, Int J Biochem Cell Biol 39:606-14.
Otoguro et al., 1988, J Antibiot (Tokyo) 41:573-5.
Pipano, 2002, Israel Journal of Veterinary Medicine 58:2-3.
Raj et al., 2003, Bioorg Med Chem 11:1015-9.
Tomlinson et al., 2009, Infect Disord Drug Targets 9, 327-343.
Tomlinson and Watowich, 2011, Antiviral Res 89:127-35.
Tomlinson and Watowich, 2008, Biochemistry 47:11763-70.
Tomlinson et al., 2009, Antiviral Res 82, 110-114.
Wagstaff et al., 2011, J Biomol Screen 16:192-200.
Xie et al., 2008, Toxicol In Vitro 22:261-6.
Yates and Wolstenholme, 2004, Int J Parasitol 34:1075-81.
Yip et al., 2006, Mol Cancer Ther 5:2234-40.
Yin et al., 2006, Bioorg Med Chem Lett 16:40-3.
Yin et al., 2006, Bioorg Med Chem Lett 16, 36-39.
Yang et al., 2007, PLos One 2, e428.
Yusof et al., 2000, J Biol Chem 275, 9963-9969.
Chambers et al., 1993, J Virol 67:6797-807.
Robin et al., Structure of West Nile Virus NS3 Protease: Ligand Stabilization of the Catalytic Conformation. J. Mol. Biol. 385: 1568-1577 (2009).

* cited by examiner

*Primary Examiner* — Marcela M Cordero Garcia
*Assistant Examiner* — Kaipeen Yang

(57) ABSTRACT

The present invention concerns methods and compositions involving small molecule inhibitors for the treatment or prophylaxis of flavivirus infection, such as dengue virus and West Nile virus.

12 Claims, 6 Drawing Sheets

A. B. C. D. E.

SMALL-MOLECULE INHIBITORS OF DENGUE AND WEST NILE VIRUS PROTEASES

PRIORITY CLAIM

This application claims priority to U.S. Provisional Patent Application Ser. No. 61/449,492 filed Mar. 4, 2012, which is incorporated herein by references in its entirety.

STATEMENT REGARDING FEDERALLY FUNDED RESEARCH

This invention was made with government support under 1R21AI066160-01A2 awarded by the NIH/NIAID. The government has certain rights in the invention.

REFERENCE TO SEQUENCE LISTING

None.

BACKGROUND

I. Field of the Invention

The present invention relates generally to the fields of virology and therapeutics. More particularly, it concerns small molecule inhibitors of Dengue and West Nile virus protease for treating flavivirus infections.

II. Description of Related Art

*Flavivirus* is a genus of the family Flaviviridae. This genus includes the West Nile virus, dengue virus, Tick-borne Encephalitis Virus, Yellow Fever Virus, and several other viruses that may cause encephalitis.

Dengue virus (DENV) is a mosquito-borne virus that causes significant disease worldwide. Endemic in more than 100 countries, DENV is estimated to cause 50 million infections each year. DENV infections can result in serious disease including dengue fever (DF), dengue hemorrhagic fever (DHF), dengue shock syndrome (DSS) and even death. Complicating matters further is the fact that DENV exists as four separate serotypes (DEN1V, DEN2V, DEN3V, and DEN4V) with infection by one serotype not providing protection from infections by the other serotypes. Furthermore, evidence suggests that subsequent infections by different serotypes may increase the probability of developing the more serious forms of the disease like DHF and DSS (Alvarez, 2006, Am J Trop Med Hyg 75:1113-7; Halstead, 2003, Adv Virus Res 60:421-67). According to the World Health Organization, DENV is considered to be the most important mosquito-borne viral disease in the world. Unfortunately, there are no vaccines approved to prevent DENV infection, and no approved antiviral drugs to treat the disease.

Every year, it is estimated that there are 50-100 million dengue virus infections with ~1.5 million documented cases of dengue fever, and ~500,000 cases of dengue hemorrhagic fever and shock syndrome. Reported cases increase annually. Approximately 40% of the world's population is at risk of dengue infection from living in regions endemic with the virus.

In 1999, West Nile virus emerged in the USA and has successfully spread across the entire country and into Canada, Mexico, and Central and South America. In 2007, the U.S. Centers for Disease Control reported 3,630 clinical cases in the USA, with 2,350 cases of West Nile fever, 1,217 cases of meningitis or encephalitis, and 124 fatalities. There are no vaccines or antiviral therapies approved for use in humans. Other regions at risk include Asia, Africa, Europe, and the Middle East.

DENV is an enveloped, positive-strand RNA virus whose ~11 Kb genome is transcribed as a single polyprotein (See Tomlinson et al., 2009, Antiviral Res 82:110-4) including the three structural (capsid, pre-m, and envelope) proteins at its 5' end followed by seven nonstructural proteins (Fields et al., 1996, Field's Virology, Third Edition, third ed. Lippincott Williams & Wilkins, Philadelphia). The N-terminal 180 residues of the NS3 protein encode the viral protease (Chambers et al., 1993, J Virol 67:6797-807) and ~40 residues from the central hydrophilic domain of the NS2B protein (Yusof et al., 2000, J Biol Chem 275:9963-9) encode the protease cofactor (Leung et al., 2001, J Biol Chem 276:45762-71). Along with cellular proteases, the NS2B-NS3 protease complex (NS2B-NS3pro) is responsible for cleavage of the viral polyprotein (Cahour et al., 1992, J Virol 66:1535-1542) and has been shown to be required for viral replication (Falgout et al., 1991, J Virol. 65:2467-2475). As such, NS2B-NS3pro provides a strategic target for inhibition in the development of flavivirus antivirals (Tomlinson et al., 2009, Infect Disord Drug Targets 9:327-43). Several groups have utilized in vitro protease assays to test potential inhibitors (Chanprapaph et al., 2005, Biochem Biophys Res Commun 330:1237-46; Tomlinson et al., 2009, Antiviral Res 82:110-4; Leung et al., 2001, J Biol Chem 276:45762-71; Yin et al., 2006, Bioorg Med Chem Lett 16:40-3).

There are no approved antiviral drugs for diseases caused by either Dengue or West Nile viruses. Currently, patients are treated with supportive care to relieve fever, pain, and dehydration. Attempts to treat West Nile disease with Ribavirin have been unsuccessful.

Therefore, there exists a need for additional vaccines or antiviral therapies to treat flavivirus infections, particularly for dengue virus and West Nile virus.

SUMMARY

Embodiments of the invention include the use of a composition comprising an effective amount of one or more NS2B-NS3 protease inhibitors. The inhibitors can be used under conditions that prevent or treat flavivirus infection in the subject. In certain aspects, the NS2B-NS3 protease inhibitor is an NS2B-NS3 protease specific inhibitor, e.g., the NS2B-NS3 protease specific inhibitor does not significantly inhibit other serine proteases such as trypsin. The term "does not significantly inhibit trypsin" refers to a compound having no detectable inhibition of trypsin or other serine proteases to a detectable $K_i$ of 200, 300, 400, 500 μM or greater.

Certain embodiments are directed to compounds with the general formula of Formula I:

Formula I

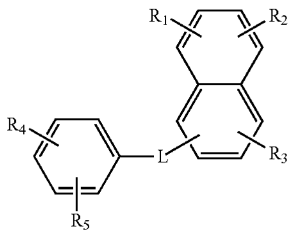

where $R_1$, $R_2$, $R_3$, $R_4$, and $R_5$ are independently hydrogen, hydroxyl, nitro, amine, or $C_1$-$C_4$ alkyl; and L is —C═N—, —N═N—, or —C(O)NH—. In certain aspects, L is at position 1, 2, 3, or 4 of the naphthalene moiety. In certain aspects, $R_1$, $R_2$, and $R_3$ are independently positioned at positions 1, 2, 3, 4, 5, 6, 7, or 8 of the naphthalene moiety. In a further aspect, $R_4$ and $R_5$ are independently positioned at positions 2, 3, 4, 5, or 6 of the phenyl moiety. In certain aspects $R_4$ and $R_5$ can be joined to form a heterocycle. In certain embodiments, $R_1$, $R_2$, and $R_3$ are independently hydroxyl. In certain aspects, the naphthalene moiety of Formula I has 1, 2, or 3 hydroxyl groups in position(s) 1, 2, 3, 4, 5, 6, 7, and/or 8 of the naphthalene moiety of formula I. In certain aspects of Formula I, the naphthalene moiety is 2-hydroxyl; 2,4-dihydroxyl; 2,6-hydroxyl; 3-hydroxyl; 3,6-dihydroxyl; 4-hydroxyl; 4,6-dihydroxyl; 5-hydroxyl; 6-hydroxyl; 6,7-dihydroxyl; 7-hydroxyl; 8-hydroxyl naphthalene.

In certain aspects, $R_4$ and $R_5$ are independently at positions 2, 3, 4, 5, or 6 of the phenyl moiety of formula I. In certain aspects, $R_4$ and $R_5$ are at positions 2 and 4, 2 and 5, or 3 and 4, respectively. In certain aspects $R_4$ and $R_5$ are nitro; $R_4$ is hydroxyl and $R_5$ is nitro; $R_4$ is nitro and $R_5$ is hydroxyl; $R_4$ and $R_5$ are hydroxyl; $R_4$ and $R_5$ are hydroxyl that are further linked by a methyl, ethyl, propyl, or butyl, group to form a heterocycle; $R_4$ is hydroxyl and $R_5$ is $C_1$-$C_4$ alkyl; and $R_4$ is $C_1$-$C_4$ alkyl and $R_5$ is hydroxyl.

In certain aspects, L is at position 1, 2, 3, 4, 5, 6, 7, or 8 of the naphthalene moiety. In certain aspects, L is at position 1 or 2 of the naphthalene moiety of Formula I.

Certain embodiments are directed to compounds that include:

| Compound | Structure | Protease inhibited in Knock-down | Denpro Ki1 (μM) | Denpro Ki2 (μM) | WNpro Ki1 (μM) | WNpro Ki2 (μM) |
|---|---|---|---|---|---|---|
| 6A49 | 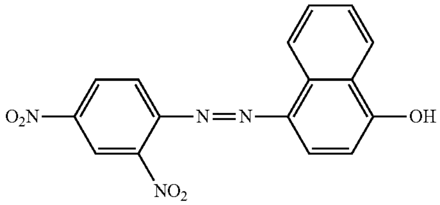 [SMILES: O=[N+]([O-])c1ccc(N=Nc2ccc(O)c3ccccc23)c([N+](=O)[O-])c1] | DENV; WNV | 15 | 10 | 34 | |
| 260 | 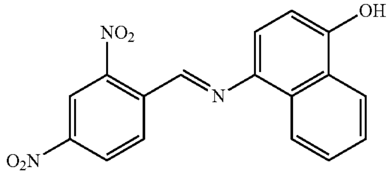 [SMILES: O=[N+]([O-])c1ccc(/C=N/c2ccc(O)c3ccccc23)c([N+](=O)[O-])c1] | DENV; WNV | 52 | 5 | 14 | 5 |
| 273 | 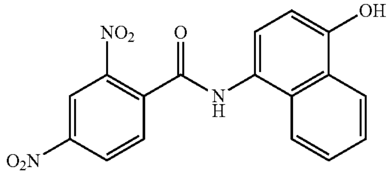 [SMILES: O=C(Nc1ccc(O)c2ccccc12)c1ccc([N+](=O)[O-])cc1[N+](=O)[O-]] | DENV; WNV | <223 | — | <169 | <186 |
| 290 | 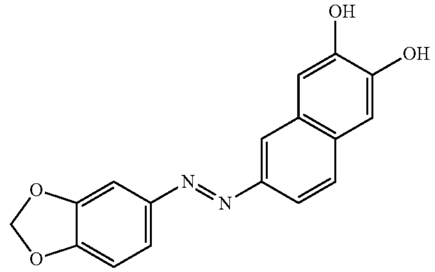 [SMILES: Oc1cc2ccc(/N=N/c3ccc4c(c3)OCO4)cc2cc1O] | DENV; WNV | — | <8.5 | — | <6 |
| 292 | 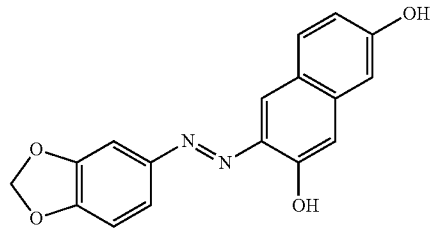 [SMILES: Oc1ccc2cc(/N=N/c3ccc4c(c3)OCO4)c(O)cc2c1] | WNV | Tbd | Tbd | Tbd | Tbd |

-continued
| Compound | Structure | Protease inhibited in Knock-down | Denpro Ki1 (μM) | Denpro Ki2 (μM) | WNpro Ki1 (μM) | WNpro Ki2 (μM) |
|---|---|---|---|---|---|---|
| 293 | 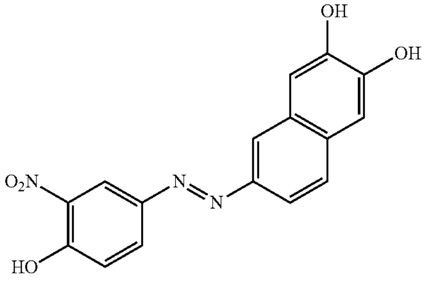 [SMILES: O=[N+]([O-])c1cc(/N=N/c2ccc3cc(O)c(O)cc3c2)ccc1O] | DENV | 432 | 29 | — | 20 |
| 296 | 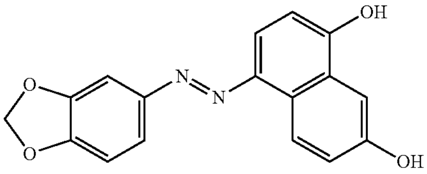 [SMILES: Oc1ccc2c(/N=N/c3ccc4c(c3)OCO4)ccc(O)c2c1] | DENV; WNV | 215 | 62 | | 116 |
| 297 | 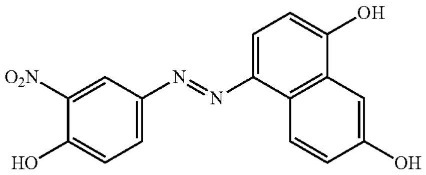 [SMILES: O=[N+]([O-])c1cc(/N=N/c2ccc(O)c3cc(O)ccc23)ccc1O] | DENV; WNV | — | 85 | — | 61 |
| 298 | 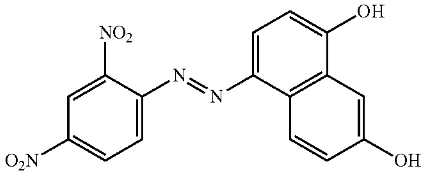 [SMILES: O=[N+]([O-])c1ccc(/N=N/c2ccc(O)c3cc(O)ccc23)c([N+](=O)[O-])c1] | DENV; WNV | 40 | 4 | 4 | 2 |
| 300 | 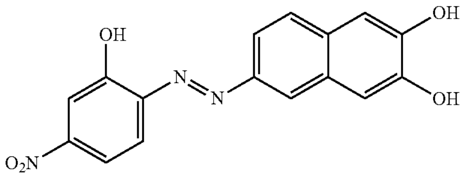 [SMILES: O=[N+]([O-])c1ccc(/N=N/c2ccc3cc(O)c(O)cc3c2)c(O)c1] | DENV; WNV | 81 | 5 | 3 | 2 |
| 301 | 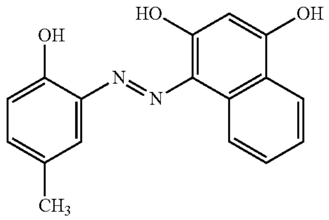 [SMILES: Cc1ccc(O)c(/N=N/c2c(O)cc(O)c3ccccc23)c1] | DENV; WNV | Tbd | Tbd | Tbd | Tbd |
| 302 | 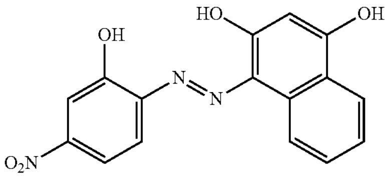 [SMILES: O=[N+]([O-])c1ccc(/N=N/c2c(O)cc(O)c3ccccc23)c(O)c1] | DENV; WNV | Tbd | Tbd | Tbd | Tbd |
*Tbd—to be determined In certain aspects, the NS2B-NS3 protease specific inhibitor may be a milbemycin analog, haematoxylin pentaacetate, methylbenzethonium salt, tyrothricin, alexidine, or an anthracene analog.

Non-limiting examples of milbemycin analog include Ivermectin, Selamectin, milbemectin, milbemycin oxime, Moxidectin, or Nemadectin. In a particular example, milbemectin analogs may include Ivermectin or Selamectin.

In particular aspects, the anthracene analog does not include 1,8-Dihydroxy-4,5-dinitroanthaquinone or orcein. Non-limiting examples of the anthracene analog may include one or more of the following:

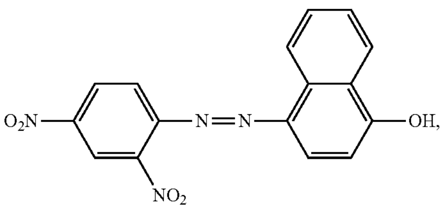
,
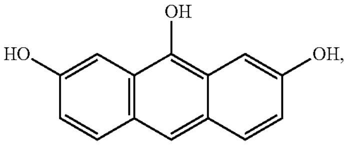
,
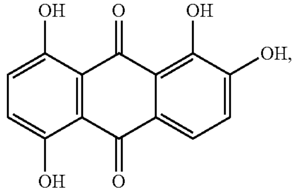
,
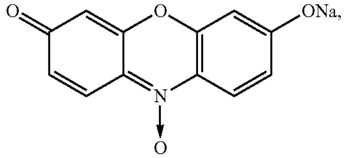
,
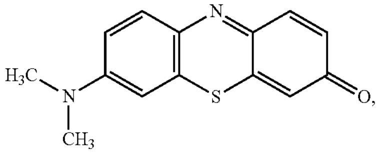
, or
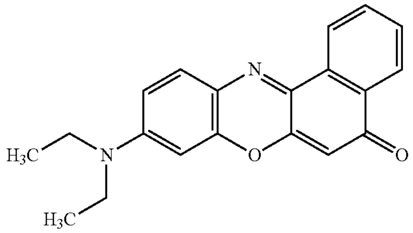

In certain aspects, the flavivirus infection may be a Dengue virus infection or a West Nile virus infection. Additional flaviviruses that can be treated or prevented include other mosquito-borne flaviviruses, such as Japanese encephalitis, Murray Valley encephalitis, St. Louis encephalitis, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

It is contemplated that any embodiment of a method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
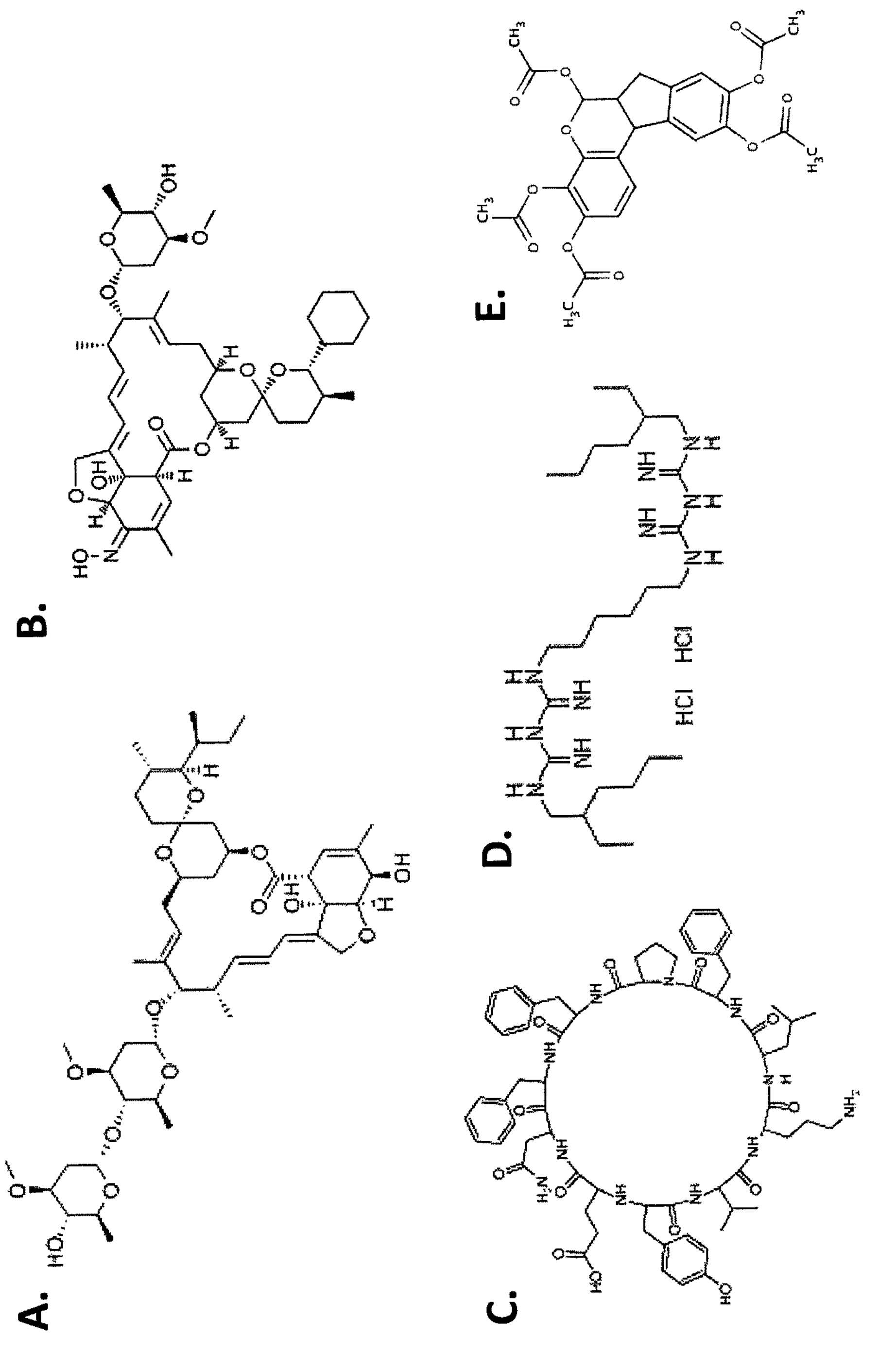
FIGS. 1A-1E. Chemical structures for lead compounds: (A) Ivermectin (MS21), (B) Selamectin (MS24), (C) Tyrothricin (MS23), (D) Alexidine hydrochloride (MS28), and (E) Haematoxylin pentaacetate.

Dengue virus (DENV), a member of the family Flaviviridae, is a significant global pathogen affecting primarily tropical and subtropical regions of the world and placing tremendous burden on the limited medical infrastructure that exists in many of the developing countries located within these regions. Recent outbreaks in developed countries including Australia (Hanna et al., 2009, Commun Dis Intell 33:198-203), France (La Ruche et al., 2010, Euro Surveill 15), Taiwan (Kuan et. al., 2010, Int J Infect Dis.), and the USA (CDC. 2010. Locally acquired Dengue—Key West, Fla., 2009-2010. MMWR Morb Mortal Wkly Rep 59:577-81) lead many researchers to believe that continued emergence into more temperate latitudes is likely. A primary concern is that there are no approved vaccines or antiviral therapies to treat DENV infections. Since the viral NS2B-NS3 protease (DEN2V NS2B-NS3pro) is required for viral replication, it provides a strategic target for the development of antiviral drugs. Dengue 2 virus (DEN2V) NS2B-NS3 protease inhibitors were identified in the present invention for the treatment and prophylaxis of dengue and West Nile virus infection and potentially other flavivirus infections. For example, six DEN2V inhibitors in Table 1 were identified that inhibited the related West Nile virus protease (WNV NS2B-NS3pro). Biochemical analyses revealed various mechanisms including competitive and mixed noncompetitive with lowest $K_i1$ values of 11±3 μM for DEN2V NS2B-NS3pro and 2±0.2 μM for WNV NS2B-NS3pro.

I. *FLAVIVIRUS*

Dengue virus and its various strains and isolates are members of the genus *Flavivirus*. The genus *Flavivirus* is a genera of the Flaviviridae family and includes the viral groups of Yellow Fever virus group, Tick-borne encephalitis virus group, Rio Bravo Group, Japanese encephalitis Group, Tyuleniy Group, Ntaya Group, Uganda S Group, Dengue Group, and Modoc Group. Members of the *Flavivirus* genus may produce a wide variety of disease states, such as fever, arthralgia, rash, hemorrhagic fever, and/or encephalitis. The outcome of infection is influenced by both the virus and host-specific factors, such as age, sex, genetic susceptibility, and/or pre-exposure to the same or a related agent. Some of the various diseases associated with members of the genus *Flavivirus* are yellow fever; dengue fever; and West Nile, Japanese, and St. Louis encephalitis. For a review of Flaviviruses see Burke and Monath (2001), which is incorporated herein by reference.

Virions of the Flaviviridae generally contain one molecule of a linear positive-sense single stranded RNA genome of approximately 10,000-11,000 nucleotides that replicates in the cytoplasm of an infected cell. Typically the 5' end of the genome has a cap and the 3' end that may or may not have a poly (A) tract. Many members of the genus *Flavivirus* are transmitted by a vector such as an insect, in many cases the insect is a mosquito.

The viral genome of the *Flavivirus* genus is translated as a single polyprotein and is subsequently cleaved into mature proteins. The proteins encoded by the virus typically consist of structural and non-structural proteins. Generally, there are three structural proteins that typically include the envelope protein (E protein) (amino acids 275-787 of GenBank accession number NP_041724, incorporated herein by reference), the core or capsid protein (C) (amino acids 1-92 of GenBank accession number NP_041724), and the pre-membrane protein (preM) (amino acids 105-223 of GenBank accession number NP_041724) (Yamshchikov et al., 2001, incorporated herein by reference). The envelope protein is approximately 496 amino acids with an approximate molecular weight of 50 kDa and is often glycosylated. The envelope protein typically contains twelve conserved cysteine residues which form six disulfide bridges. The core protein is approximately 13 kDa and is rich in arginine and lysine residues. The pre-membrane protein is approximately 10 kDa and is cleaved during or after release of the virus from infected cells. A cleavage product of the prM protein remains associated with the virion and is approximately 8 kDa and is termed the membrane protein (M). Typically, it is the carboxy terminus of prM that remains associated with the virus particle as the M protein.

Serological comparisons of West Nile virus strains have distinguished four major antigenic subtypes: a group of strains from Africa; strains from Europe and some Asian strains; strains from India; and strains of Kunjin virus from Australasia (Doherty et al., 1968; Hammam et al., 1966; Blackburn et al., 1987; Calisher et al., 1989; Morvan et al., 1990). Subsequently, analyses of nucleotide sequences identified two major genetic lineages, designated I and II, which included some subtypes and which correlated well with the antigenic groupings. Genetic lineage I included European and some African strains, Kunjin virus strains, and Indian strains; lineage II comprised only African strains (Lanctiotti et al., 1999; Jia et al., 1999; Scherret et al., 2001).

Various members of the Flaviviridae family are available through the American Type Culture Collection (Manassas Va.) under the following ATCC numbers: Dengue type 1 (VR-71), Ilheus (VR-73), Japanese encephalitis (VR-74), Murray Valley encephalitis (VR-77), Ntaya (VR-78), St. Louis encephalitis (VR-80), Uganda S (VR-81), West Nile (VR-82), Zika (VR-84), Dengue type 4 (VR-217), Dengue type 2 (VR-222), Japanese encephalitis (VR-343), Dengue type 1 (VR-344), Dengue type 2 (VR-345), Edge hill (VR-377), Entebbe bat (VR-378), Kokobera (VR-379), Stratford (VR-380), Tembusu (VR-381), Dakar bat (VR-382), Ntaya (VR-78), Banzi (VR-414), Modoc (VR-415), Rio Bravo virus (VR-416), Cowbone ridge (VR-417), Bukalasa (VR-418), Montana myotis leukoencephalitis (VR-537), Bussuquara (VR-557), Sepik (VR-906), Cowbone ridge (VR-1253), Dengue type 2 (VR-1255), Dengue type 3 (VR-1256), Dengue type 4 (VR-1257), Ilheus (VR-1258), Rio Bravo virus (VR-1263), St. Louis encephalitis (VR-1265), West Nile (VR-1267), Dengue type 4 (VR-1490), West Nile (VR-1507), and West Nile (VR-1510), each of which is incorporated herein by reference.

II. NS2B-NS3 PROTEASE

The existence of a trypsin-like serine protease domain in the N-terminal region of the flaviviral NS3 proteins was originally predicted by sequence comparisons between cellular and virus-encoded proteases. The NS2B-NS3 endopeptidases of the *Flavivirus* genus which at present comprises at least 68 known members, are now commonly designated as flavivirin (EC 3.4.21.91). The dengue virus 69 kDa NS3 protein is a multifunctional protein with a serine protease domain located within the Nterminal 167 amino acid residues and activities of a nucleoside triphosphatase (NTPase) and RNA helicase in the C-terminal moiety. A catalytic triad consisting of residues His51, Asp75 and Sen 35 was identified by site-directed mutagenesis experiments and replacement of the catalytic serine by alanine resulted in an enzymatically inactive NS3 protein. The NS3 protease is an essential component for maturation of the virus and viable virus was never recovered from infectious cDNA clones carrying mutations in the NS3 sequence which abolished protease activity. Interaction of the helicase portion of NS3 with the viral RNAdependent RNA polymerase NS5 may promote the association of the viral replicase complex to the membranes of the ER.

The DENV NS3 is a serine protease, as well as an RNA helicase and RTPase/NTPase. The protease domain consists of six β-strands arranged into two β-barrels formed by residues 1-180 of the protein. The catalytic triad (His-51, Asp-75 and Ser-135), is found between these two β-barrels, and its activity is dependent on the presence of the NS2B cofactor. This cofactor wraps around the NS3 protease domain and becomes part of the active site. The remaining NS3 residues (180-618), form the three subdomains of the DENV helicase. A six-stranded parallel β-sheet surrounded by four α-helices make up subdomains I and II, and subdomain III is composed of 4 α-helices surrounded by three shorter α-helices and two antiparallel β-strands The presence of a small activating protein or co-factor is a prerequisite for optimal activity of the flaviviral NS3 proteases with their natural polyprotein substrates. Although the dengue virus NS3 protease exhibits NS2B independent activity with model substrates for serine proteases, enzymatic cleavage of dibasic peptides is markedly enhanced with the NS2B-NS3 co-complex and the presence of the NS2B activation sequence is indispensable for the cleavage of polyprotein substrates in vitro. The initial characterization of the co-factor requirement for the dengue virus NS3 protease had revealed that the minimal region necessary for protease activation was located in a 40-residue hydrophilic segment of NS2B.

III. NOVEL NS2B-NS3 PROTEASE INHIBITORS

In certain aspects of the present invention, certain NS2B-NS3 protease inhibitors are provided for the treatment and prophylaxis of flavivirus infections. Exmplers of chemical structures of novel NS2B-NS3 protease inhibitors are depicted in FIG. 1.

The protease inhibitor may be milbemycin analog, such as Ivermectin, Selamectin, milbemectin, milbemycin oxime, Moxidectin, or Nemadectin. The milbemycins are a group of macrolides chemically related to the avermectins and were first isolated in 1972 from *Streptomyces hygroscopicus*. They are used in veterinary medicine as antiparasitic agents against worms, ticks and fleas. Milbemycins (Formula 1) are products of fermentation by *Streptomyces* species. They have a similar mechanism of action, but a longer half-life than the avermectins. They open glutamate sensitive chloride channels in neurons and myocytes of invertebrates, leading to hyperpolarisation of these cells and blocking of signal transfer.

Formula II

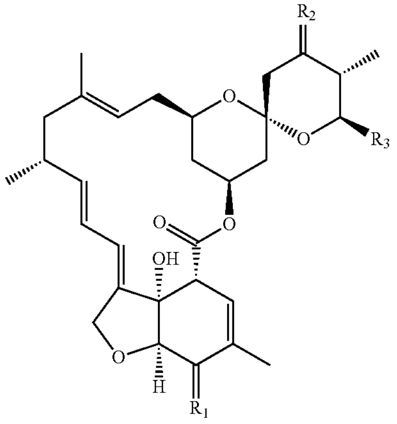

| Name | $=R_1$ | $=R_2$ | $—R_3$ |
|---|---|---|---|
| Milbemectin | —H, (β)-OH | —H, —H | $—CH_3$:$—CH_2CH_3$ = 3:7 |
| Milbemycin oxime | =NOH | —H, —H | $—CH_3$:$—CH_2CH_3$ = 3:7 |
| Moxidectin | —H, (β)-OH | $=NOCH_3$ | (Z)—$C(CH_3)$=CH—$CH(CH_3)_2$ |
| Nemadectin | —H, (β)-OH | —H, (α)-OH | (Z)—$C(CH_3)$=CH—$CH(CH_3)_2$ |

Ivermectin (MS21) is a macrocyclic lactone derived from *Streptomyces avermitilis* (FIG. 1A). Ivermectin (22,23-dihydroavermectin B1a+22,23-dihydroavermectin B1b) is a broad-spectrum antiparasitic avermectin medicine. It is sold under brand names Stromectol in the United States, Mectizan in Canada by Merck and Ivexterm in Mexico by Valeant Pharmaceuticals International.

In humans, Ivermectin is most often used to treat roundworm infections such as strongyloidiasis, onchocerciasis (river blindness), and others. Interestingly, it has recently been published that Ivermectin also blocks nuclear import of HIV integrase (Wagstaff et al., 2011, J Biomol Screen 16:192-200). The determined mechanism of action associated with roundworm infection is that it activates glutamate-gated chloride channels, enhancing inhibitory neurotransmission thus interfering with muscle and nervous system function of the helminthes (Yates and Wolstenholme, 2004, Int J Parasitol 34:1075-81). In canines, it is used to kill larval heartworms and sterilize adult heartworms thus preventing serious infection. Ivermectin can be administered by injection, but is also formulated as a tablet that is taken by mouth as a single dose, though in some cases, multiple treatments are required. Since 1987, Merck has donated >697 million treatment doses of the drug to countries that cannot afford it for the treatment and prevention of river blindness (Ogoussan and Hopkins, 2010, Mectizan((R)) procurement and delivery for onchocerciasis mass drug administration programmes. Acta Trop). Though its toxicity is documented (Molinari et al., 2009, J Hazard Mater 165:1074-82; Xie et al., 2008, Toxicol In Vitro 22:261-6) for the therapeutic concentration for onchocerciasis, it needs to be evaluated at the higher concentrations required for DEN2V and WNV protease inhibition. Therapeutic use of Ivermectin for DEN2V infections may be worth pursuing as means are already in place to distribute free treatment in countries that are also endemic with dengue virus.

Selamectin (MS24), a related macrolitic lactone, is also derived from *Streptomyces avermitilis* (FIG. 1B). Currently, it is marketed by Pfizer as a topical broad-spectrum parasiticide used in dogs and cats to control fleas, ear mites, heartworms, hookworms, and roundworms. It is not, however approved for human use. Like Ivermectin, Selamectin is administered orally, but can also be absorbed through the skin, enter the blood, intestines, and sebaceous glands, and kill parasites that feed on blood. Selamectin is reported to have a high safety profile in cats and dogs (breeding animals as well as kittens and puppies) with both oral and topical administration (Pipano, 2002, Israel Journal of Veterinary Medicine 58:2-3) exceeding that of the related Ivermectin, and may also be worth pursuing as a DEN2V or WNV protease inhibitor. In addition, a related group of macrolides, the milbemycins, could also be evaluated for DEN2V NS2B-NS3pro inhibition.

Tyrothricin (MS23), synthesized by the bacteria *Aneurinibacillis migulanus*, is a mixture of antibiotics, gramicidins A, B, C, and S, and tyrocidins (FIG. 1C). It is reported to be a very effective antibiotic against both gram-positive and gram-negative bacteria (Mogi and Kita, 2009, Cell Mol Life Sci 66:3821-6) as well as pathogenic fungi and nematodes (Otoguro et al., 1988, J Antibiot (Tokyo) 41:573-5). It's mechanism of inhibition for both DEN2V and WNV proteases was purely competitive which is not too surprising as the peptide includes a lysine which is a preferred substrate residue which interacts with the P1 pocket of the active sites of both DEN2V and WNV proteases. Unfortunately, gramicidin S is hemolytic, so it is limited to topical use (Mogi and Kita, 2009, Cell Mol Life Sci 66:3821-6). As Tyrothricin is a mixture of these gramicidins, it may be possible to synthesize a derivative that lacks the currently observed hemolytic properties. Additionally, before it could be developed for therapeutic use for DENV and WNV infections, cell permeability would have to be addressed.

Alexidine hydrochloride (MS28) (FIG. 1D), is a potent antibiotic that has been used in mouthwashes (McDonnell and Russell, 1999, Clin Microbiol Rev 12:147-79), and most recently reported as a potential cancer therapeutic (Yip et al., 2006, Mol Cancer Ther 5:2234-40). Toxicity studies in cells, however, demonstrated low micromolar $ED_{50}$ (cell viability reduced by 50%) values (Yip et al., 2006, Mol Cancer Ther 5:2234-40).

Haematoxylin pentaacetate (MS5), is included in the "natural products" group of the MicroSource library (FIG. 1E). Though it has been reported to be an effective transactylase inhibitor in microsomal assays (Raj et al., 2003, Bioorg Med Chem 11:1015-9), its toxicity in cells has to our knowledge not been studied. In our assays, it was difficult to determine inhibition constants for this compound. Haematoxylin pentaacetate is known to oxidize over time and changes color as the pH of the environment changes. It may also be that the compound precipitates over time. Experiments indicate that upon addition of the compound to the enzyme and substrate, decrease in signal is very dramatic. However, as time passes, color changes, and the inhibition is less. Allowing the compound to incubate with the cleavage buffer overnight (resulting in complete oxidation) produced no observable inhibition in single-point knock-down assays with either protease. It should be noted that AMC controls were implemented at all stages, and the color changes did not produce an AMC interaction. It may worth exploring an "unoxidizable" form of this compound as the initial inhibition is significant.

A list of small molecule chemical entities (termed invention) that inhibit dengue and/or West Nile virus proteases (compounds are all commercially available) is presented below. These compounds have been tested and demonstrated inhibition of both dengue and West Nile virus proteases. Efficacy studies for several compounds have been completed to determine EC50 (concentration at which virus production is decreased by 50%). Cell culture toxicity studies for several compounds have been performed to determine the CC50 (concentration at which half of the cells die). Analogs of these compounds may show increased activity and decreased toxicity.

| | | Ki1 (uM) (from biochemical protease inihibition experiments) | |
|---|---|---|---|
| In-house name | Chemical structure | Dengue 2 virus NS2B-NS3 | West Nile virus NS2B-NS |
| 6A42 | 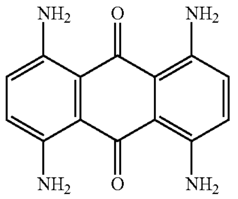 [SMILES: Nc1ccc(N)c2c1C(=O)c1c(N)ccc(N)c1C2=O] | 158 | — |
| 6A45 | 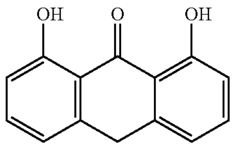 [SMILES: O=C1c2c(O)cccc2Cc2cccc(O)c21] | 47 | 2 |

-continued
| In-house name | Chemical structure | Ki1 (uM) (from biochemical protease inihibition experiments) Dengue 2 virus NS2B-NS3 | West Nile virus NS2B-NS |
|---|---|---|---|
| 6A47 | 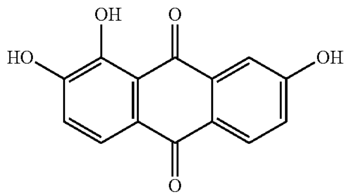 [SMILES: O=C1c2ccc(O)cc2C(=O)c2c1ccc(O)c2O] | 215 | — |
| 6A49 | 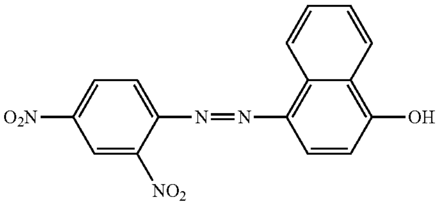 [SMILES: O=[N+]([O-])c1ccc(N=Nc2ccc(O)c3ccccc23)c([N+](=O)[O-])c1] | 15 | 34 |
| 6A60 | 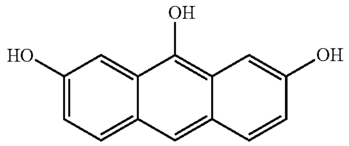 [SMILES: Oc1ccc2cc3ccc(O)cc3c(O)c2c1] | 7 | 11 |
| 6A61 | 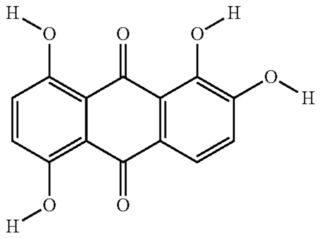 [SMILES: O=C1c2ccc(O)c(O)c2C(=O)c2c(O)ccc(O)c21] | 72 | 31 |
| 6A62 | 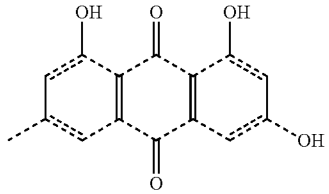 | 508 | 1035 |
| 9A3 | 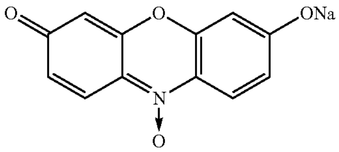 | 82 | 72 |
| 9A4 | 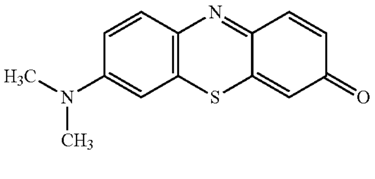 [SMILES: CN(C)c1ccc2nc3ccc(=O)cc-3sc2c1] | 359 | 431 |

-continued

| In-house name | Chemical structure | Ki1 (uM) (from biochemical protease inihibition experiments) Dengue 2 virus NS2B-NS3 | West Nile virus NS2B-NS |
|---|---|---|---|
| 9A6 | 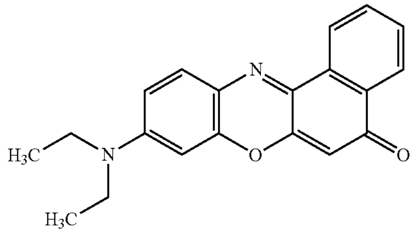 [SMILES: CCN(CC)c1ccc2nc3c4ccccc4c(=O)cc-3oc2c1] | 53 | 47 |

IV. ANTHRACENE-BASED DEN2V NS2B-NS3 PROTEASE INHIBITORS

Dengue virus is an important insect-borne pathogen with significant impact on global health, and thus ranks as an important target for developing small molecule drug candidates. A number of strategies have been suggested for the development of dengue antivirals (Tomlinson et al., 2009, Infect Disord Drug Targets 9, 327-343) including targeting dengue structural proteins (Hrobowski et al., 2005, Virol J 2, 49; Marks et al., 2001, J Med Chem 44, 2178-2187; Modis et al., 2003, Proc Natl Acad Sci USA 100, 6986-6991; Yang et al., 2007, PLos One 2, e428), and nonstructural proteins such as the NS5 polymerase (Latour et al., 2010, Antiviral Res 87, 213-222) and the NS2B-NS3 protease (Chanprapaph et al., 2005, Biochem Biophys Res Commun 330, 1237-1246; Ganesh et al., 2005, Bioorg Med Chem 13, 257-264; Leung et al., 2001, J Biol Chem 276, 45762-45771; Mueller et al., 2008, Antimicrob Agents Chemother 52, 3385-3393; Tomlinson et al., 2009, Antiviral Res 82, 110-114; Yin et al., 2006, Bioorg Med Chem Lett 16, 36-39; Yusof et al., 2000, J Biol Chem 275, 9963-9969). Viral proteases are a particularly attractive drug targets, in particular since HIV protease inhibitors have been licensed (Hsu et al., 2006, Curr Pharm Des 12, 1301-1314) and inhibitors of hepatitis C virus (Lamarre et al., 2003, Nature 426, 186-189) and human rhinovirus (Hayden et al., 2003, Antimicrob Agents Chemother 47, 3907-3916) proteases have entered clinical trials.

Anthracene is a solid polycyclic aromatic hydrocarbon consisting of three fused benzene rings. It is a component of coal-tar. Anthracene is used in the production of the red dye alizarin and other dyes. Anthracene is colorless but exhibits a blue (400-500 nm peak) fluorescence under ultraviolet light.

The activity of several analogs of ARDP0006 were analyzed to better understand the molecular determinants that were associated with inhibition activity. Rigorous kinetic analyses provided both accurate inhibition constants and mechanisms of inhibition. Interestingly, 6 of 8 analogs exhibited a mixed noncompetitive mechanism of inhibition with both $K_i1$ and $K_i2$ values, which suggested these inhibitors bound the apoenzyme (E) and the enzyme-substrate (ES) complex (see scheme 1). The observation of a non-competitive mode of inhibition implied that there was a substrate-dependent binding event that could inhibit the protease even at high substrate concentrations; this could have significant in vivo ramifications since the protease would be inhibited during high levels of replication (high levels of polyprotein substrate). Alternatively, the observed uncompetitive component of inhibition could be an artifact of the AMC-coupled substrate. Evidence for this latter interpretation was observed in trypsin inhibition kinetic studies using substrates with either chromogenic or fluorogenic leaving groups. In these experiments, some inhibitors prevented cleavage of the fluorogenic substrate (via an uncompetitive mechanism) but not the chromogenic substrate (data not shown). Thus, this dengue protease inhibition study utilized $K_i1$ values (competitive and mixed noncompetitive mechanisms) to develop a SAR, since the $K_i2$ values may have included uncompetitive interactions with the ES complex and/or substrate-dependent artifacts due to interactions between inhibitors and the AMC moiety. Rigorous kinetic analyses, as opposed to simple determination of $IC_{50}$ values, were necessary to decide which compounds were incorporated into SAR and developed as antiviral leads.

SAR and docking studies of anthracene-based compounds suggested potential interactions between the NS2B-NS3 protease and functional groups flanking the inhibitor scaffold. Interactions involved conserved catalytic and active site residues. Highest inhibitory activity was associated with hydroxyl groups situated on a common edge of all three anthracene rings. Functional groups on the opposite (i.e., exposed) edge of the anthracene scaffold correlated with reduced activity. Screening of a limited number of commercially-available anthracene-based "second series" analogs resulted in a sixty-fold decrease in the $K_i1$ value relative to lead compound ARDP0006 and an increase in selectivity relative to trypsin inhibition (Table 1, 4). The above SAR and structural models can guide rational modification of the anthracene scaffold to develop selective sub-micromolar binding inhibitors.

RNA virus such as DENV were estimated to have a mutation rate between $10^{-3}$ and $10^{-5}$ per base per generation (Drake, 1993, Proc Natl Acad Sci USA 90, 4171-4175). The emergence of drug resistant strains are well documented in HIV (Trono et al., 2010, Science 329, 174-180) and influenza (Holmes, 2010, Science 328, 1243-1244), and have resulted in the eventual ineffectiveness of some antiviral therapeutics. The emergence of drug-resistant strains is an issue that will need to be addressed before DENV antiviral drugs are approved for use in humans. One promising approach to this issue will be to develop dengue antivirals that interact with conserved residues of the protease, thereby increasing the likelihood that drug-resistant mutations will be detrimental to the fitness and survival of the mutated virus. Since the above anthracene-based inhibitors were predicted to interact with conserved residues of the catalytic triad and active site, drugs developed from these compounds may delay the emergence of drug-resistant dengue viruses. Moreover, since these residues were invariant in all dengue virus serotypes and in distant flaviviruses such as West Nile, Japanese encephalitis, and yellow fever viruses, these inhibitors may serve as the basis for developing broad-spectrum antivirals.

From SAR and structural models, the inventors developed a design strategy from which to proceed with inhibitor improvement. Comprehensive kinetic studies identified selective low molecular weight analogs with an ~60-fold increase in inhibition (as evidenced by decreased $K_i1$) over the parent compound. Future studies will include cell culture and small animal studies.

V. CHEMICAL DEFINITIONS

Various chemical definitions related to AMPAR modulating compounds are provided as follows.

As used herein, “predominantly one enantiomer” means that the compound contains at least 85% of one enantiomer, or more preferably at least 90% of one enantiomer, or even more preferably at least 95% of one enantiomer, or most preferably at least 99% of one enantiomer. Similarly, the phrase “substantially free from other optical isomers” means that the composition contains at most 5% of another enantiomer or diastereomer, more preferably 2% of another enantiomer or diastereomer, and most preferably 1% of another enantiomer or diastereomer. In certain aspects, one, both, or the predominant enantiomer forms or isomers are all covered.

As used herein, the term “nitro” means —$NO_2$; the term “halo” or “halogen” designates —F, —Cl, —Br, or —I; the term “mercapto” means —SH; the term “cyano” means —CN; the term “azido” means —$N_3$; the term “silyl” means —$SiH_3$, and the term “hydroxy” means —OH.

The term “alkyl,” by itself or as part of another substituent, means, unless otherwise stated, a linear (i.e. unbranched) or branched carbon chain of 1, 2, 3, 4, 5, 6, 7, 8, 9, or 10 carbons, which may be fully saturated, monounsaturated, or polyunsaturated. An unsaturated alkyl group includes those having one or more carbon-carbon double bonds (alkenyl) and those having one or more carbon-carbon triple bonds (alkynyl). The groups, —$CH_3$ (Me, methyl), —$CH_2CH_3$ (Et, ethyl), —$CH_2CH_2CH_3$ (n-Pr, n-propyl), —$CH(CH_3)_2$ (iso-Pr, isopropyl), —$CH_2CH_2CH_2CH_3$ (n-Bu, n-butyl), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), are all non-limiting examples of alkyl groups.

The term “heteroalkyl,” by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, S, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —$CH_2F$, —$CH_2Cl$, —$CH_2Br$, —$CH_2OH$, —$CH_2OCH_3$, —$CH_2OCH_2CF_3$, —$CH_2OC(O)CH_3$, —$CH_2NH_2$, —$CH_2NHCH_3$, —$CH_2N(CH_3)_2$, —$CH_2CH_2Cl$, —$CH_2CH_2OH$, $CH_2CH_2OC(O)CH_3$, —$CH_2CH_2NHCO_2C(CH_3)_3$, and —$CH_2Si(CH_3)_3$.

The terms “cycloalkyl” and “heterocyclyl,” by themselves or in combination with other terms, means cyclic versions of “alkyl” and “heteroalkyl”, respectively. Additionally, for heterocyclyl, a heteroatom can occupy the position at which the heterocycle is attached to the remainder of the molecule. Examples of cycloalkyl groups include cyclopropyl, cyclobutyl, cyclopentyl, cyclohexyl, and cycloheptyl groups. Examples of heterocyclic groups include indole, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

The term “aryl” means a polyunsaturated, aromatic, hydrocarbon substituent. Aryl groups can be monocyclic or polycyclic (e.g., 2 to 3 rings that are fused together or linked covalently). The term “heteroaryl” refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 4-azaindole, 5-azaindole, 6-azaindole, 7-azaindole, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, $(alkyl)_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, $(alkyl)_2$amino, alkylsulfinyl, alkylsulfonyl, arylsulfonyl, unsubstituted cycloalkyl, unsubstituted heterocyclyl, unsubstituted aryl, or unsubstituted heteroaryl. Examples of optional substituents include, but are not limited to: —OH, oxo (═O), —Cl, —F, Br, $C_{1-4}$alkyl, phenyl, benzyl, —$NH_2$, —$NH(C_{1-4}alkyl)$, —$N(C_{1-4}alkyl)_2$, —$NO_2$, —$S(C_{1-4}alkyl)$, —$SO_2(C_{1-4}alkyl)$, —$CO_2(C_{1-4}alkyl)$, and —$O(C_{1-4}alkyl)$.

The term “alkoxy” means a group having the structure —OR', where R' is an optionally substituted alkyl or cycloalkyl group. The term “heteroalkoxy” similarly means a group having the structure —OR, where R is a heteroalkyl or heterocyclyl.

The term “amino” means a group having the structure —NR'R", where R' and R" are independently hydrogen or an optionally substituted alkyl, heteroalkyl, cycloalkyl, or heterocyclyl group. The term “amino” includes primary, secondary, and tertiary amines.

The term “oxo” as used herein means an oxygen that is double bonded to a carbon atom.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

VI. PHARMACEUTICAL FORMULATIONS AND ADMINISTRATION OF NS2B-NS3 PROTEASE INHIBITORS

With regard to treatment of a patient, an "effective amount" of an NS2B-NS3 protease inhibitor, or a pharmaceutical composition containing a NS2B-NS3 protease inhibitor, is an amount sufficient to inhibit NS2B-NS3 protease.

Pharmaceutical compositions and formulations of the NS2B-NS3 protease inhibitor can be administered by direct injection into infected cell, tissue or organ, or administered parenterally, intravenously, intradermally, intramuscularly, transdermally, intraperitoneally, intrathecally, or per os.

For injection, solutions of the active compounds as free base or pharmacologically acceptable salts can be prepared, for example, in water, glycerol, liquid polyethylene glycols, and mixtures thereof and in oils, to form a solution or suspension. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions can be prepared by incorporating the active compounds in the required amount in the appropriate solvent with various of the other ingredients enumerated above, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions may be administered in a manner compatible with the dosage formulation and in such amount as is therapeutically effective. The formulations are easily administered in a variety of dosage forms such as injectable solutions, drug release capsules and the like. Methods of preparing formulations will be apparent to those skilled in the art (for example, see Remington's Pharmaceutical Sciences" 15th Edition).

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared The routes of administration may vary, naturally, with the location and nature of the damage, and include, e.g., intradermal, transdermal, parenteral, intravenous, intramuscular, intranasal, subcutaneous, percutaneous, intratracheal, intraperitoneal, perfusion, lavage, direct injection, and oral administration and formulation.

The NS2B-NS3 protease inhibitor can be given in a single dose, or multiple doses. Continuous administration also may be applied where appropriate. The dose of a therapeutic composition via continuous perfusion may be equivalent to that given by a single or multiple injections, adjusted over a period of time during which the perfusion occurs. The amount of NS2B-NS3 protease inhibitor administered may be dependent on the subject being treated, the subject's weight, the manner of administration, and the judgment of the physician. Treatment regimens may vary as well, and often depend on the type of nervous system damage, location of the damage, disease progression, and health and age of the patient.

In some embodiments, an NS2B-NS3 protease inhibitor may be administered to a patient systemically or by local injection. Systemic administration can be by intravenous or intraperitoneal delivery. The NS2B-NS3 protease inhibitor can be administered to reach a circulating level of about 2 to 20 mg/ml in blood, or a dose of about 100-300 mg can be delivered to a patient.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Novel Dengue NS3 Protease Inhibitors

Kinetic Analyses of DEN2V NS2B-NS3pro Inhibitors.

Figure 2:
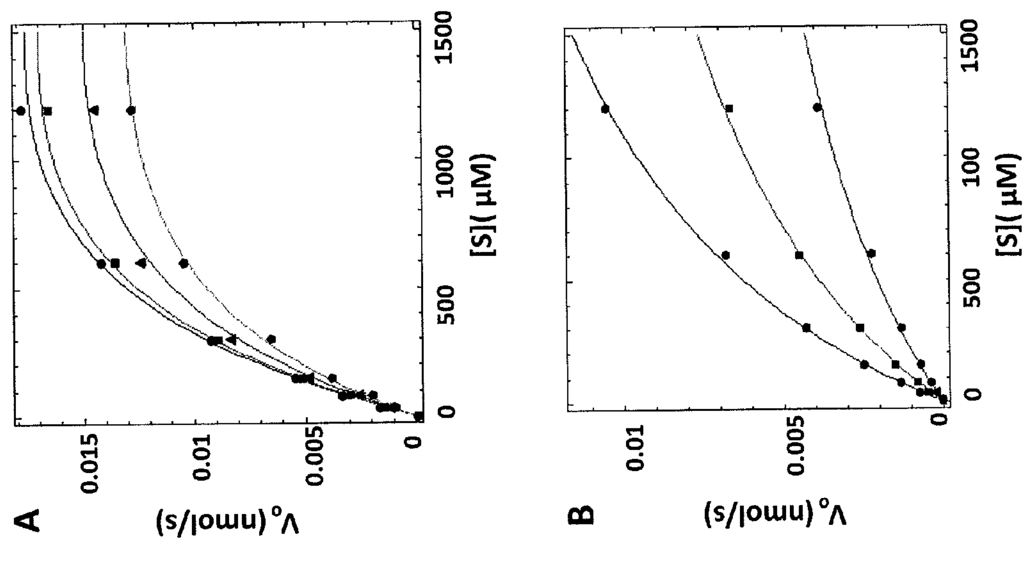
FIGS. 2A-2B. Representative curves for lead compounds (A) MS22 (Methylbenzethonium choloride) and (B) MS28 (Alexidine hydrochloride) demonstrating inhibition of DEN2V NS2B-NS3 pro. Concentrations of MS22 tested were 0 (circles), 10 (squares), 50 (triangles), and 100 (pentagons) μM. Concentrations of MS28 tested were 0 (circles), 30 (squares), and 100 (pentagons) μM. Data was analyzed with the program Dynafit.

Experiments to determine DEN2V protease kinetics were performed with substrate BOC-GRR-AMC concentrations ranging from 0 to 5 mM (well above $K_m$). Kinetic analyses with varied ranges of substrate concentrations produced very similar kinetic parameters, however, error estimates were slightly lower for experiments using the largest range of substrate concentrations. $K_m$ and $K_{cat}$ were thus constrained to those values obtained from the higher substrate concentration experiments with kinetic parameters essentially the same for all kinetic assays; $K_m$=921±68 μM, $K_{cat}$=0.05±0.002 $s^{-1}$. To determine mechanism of inhibition and inhibition constants for the HTS-identified "hits," detailed kinetic analyses were completed for each compound with DEN2V NS2B-NS3pro. Increasing concentrations of each inhibitor were tested for protease inhibition with substrate concentrations ranging from 0 to 1.2 mM, and with $K_m$ and $K_{cat}$ constrained to previously determined values as described above. For each substrate concentration, initial reaction velocities were determined and plotted using GraphPad Prism (GraphPad Software, San Diego, Calif.). Errors associated with initial velocity measurements were consistently <2%. Kinetic analyses for the velocity vs. substrate concentration data were performed using the program Dynafit (Biokin, Watertown, Mass.) (Kuzmic, 1996, Anal Biochem 237:260-73). Kinetic parameters for each model were optimized to provide the best global fit to the experimental data. Final model selection was based on fitting accuracy, parameter errors, and model discrimination analysis within the Dynafit program. Kinetic analyses of the compounds clearly indicated that they demonstrated inhibition of DEN2V NS2B-NS3pro. Selected models demonstrated excellent fits to the experimental data as indicated by representative curves for MS22 (FIG. 2A) and MS28 (FIG. 2B). Mechanisms were determined to be mixed noncompetitive for all but one compound, MS23, which demonstrated competitive inhibition. Inhibition mechanisms with computed model parameters are shown in Table 1.

TABLE 1

| ID | Common Name | Mechanism | $K_i1$ (μM) | $K_i2$ (μM) |
|---|---|---|---|---|
| MS5 | Haematoxylin pentaacetate | Mixed | 16 ± 7 | 5 ± 0.7 |
| MS21 | Ivermectin | Mixed | 79 ± 21 | 35 ± 4 |

TABLE 1-continued

| ID | Common Name | Mechanism | $K_i1$ (μM) | $K_i2$ (μM) |
|---|---|---|---|---|
| MS22 | Methylbenzethonium chloride | Mixed | 322 ± 81 | 160 ± 39 |
| MS23 | Tyrothricin | Competitive | 12 ± 1.5 | — |
| MS24 | Selamectin | Mixed | 63 ± 18 | 45 ± 8 |
| MS28 | Alexidine hydrochloride | Mixed | 41 ± 3 | 84 ± 16 |

Inhibition of WNV NS2B-NS3pro.

Due to the structural similarity between DEN2V and WNV NS2B-NS3 proteases, DEN2V NS2B-NS3pro inhibitors were tested for activity against WNV NS2B-NS3pro. Assays were conducted similarly to the DEN2V NS2B-NS3pro assays described above with $K_m$ and $K_{cat}$ determined from experiments utilizing a wide range of substrate concentrations (up to 5 mM), $K_m$=489±68 μM and $K_{cat}$=0.04±0.004 $s^{-1}$. All demonstrated activity against WNV NS2B-NS3pro (Table 2), though compound MS5 (Haematoxylin pentaacetate), did not provide reproducible inhibition constants (explained later). Compounds demonstrated the same inhibition mechanisms in both proteases, revealing similar inhibition constants with slightly better inhibition of WNV NS2B-NS3pro in some cases. While DEN2V and WNV are closely related (same genus) and the NS2B-NS3 proteases are structurally similar, the sequence identity of the NS3 protease domain is only ~50% (Erbel et al., 2006, Nat Struct Mol Biol 13:372-3). By validating activity of DEN2V NS2B-NS3pro against WNV NS2B-NS3pro, a more phylogenetically distant flavivirus than the other dengue serotypes (dengue 1, DEN1V; dengue 3, DEN3V; dengue 4, DEN4V), we can assume a high probability that the compounds will also demonstrate protease inhibition in the other more closely related dengue serotypes. We have shown in previous studies that compounds that inhibited both proteases were likely interacting with conserved residues (Tomlinson and Watowich, 2011, Antiviral Res 89:127-35). By moving forward only compounds that inhibit both viral proteases (possibly binding conserved residues), it is possible that the eventual development of drug-resistant strains could be minimized.

TABLE 2

| ID | Common Name | Mechanism | $K_i1$ (μM) | $K_i2$ (μM) |
|---|---|---|---|---|
| MS5 | Haematoxylin pentaacetate | Mixed | — | — |
| MS21 | Ivermectin | Mixed | 55 ± 18 | 16 ± 4 |
| MS22 | Methylbenzethonium chloride | Mixed | 141 ± 20 | 307 ± 80 |
| MS23 | Tyrothricin | Competitive | 2 ± 0.2 | — |
| MS24 | Selamectin | Mixed | 15 ± 9 | 28 ± 6 |
| MS28 | Alexidine hydrochloride | Mixed | 12 ± 1.2 | 28 ± 5 |

DEN2V NS2B-NS3pro Expression and Purification.

Expression and purification of the DEN2V NS2B cofactor linked to the protease domain of NS3 (NS2B-NS3pro; plasmids obtained from Dr. Siew Pheng of Novartis Institute for Tropical Diseases, Singapore) were modified from previously described protocol (Li et al., 2005, J Biol Chem 280: 28766-28774) and described in detail in a previous publication (Tomlinson and Watowich, 2011, Antiviral Res 89:127-35).

DEN2V NS2B-NS3pro Inhibition Assay.

Four compound dilution plates (each with 80 compound and 16 control wells), one enzyme plate, one control plate (either AMC or trypsin), three assay plates, and all tips required for the run were transferred to the Biomek FX (Beckman-Coulter, Brea, Calif.). The robot protocol was pre-programmed by the UTHSC core facility. Once the program was started, it took ~20 minutes to complete. After the run was complete, plates were removed, covered, shaken (Titer Plate Shaker, Lab-Line Industries) for ~30 seconds to mix, and centrifuged at low speed to remove droplets from the sides and lid. Plates were then covered and allowed to incubate for 30 minutes at room temperature so that the enzyme and compounds had time to associate. Substrate, BOC-GRR-AMC was then added (peristaltic pump) for a final concentration of 100 μM to the assay plates and 30 μM to the trypsin control plates. Plates were then allowed to incubate at room temperature for 45 minutes. Guanidine hydrochloride (1M) was then added to the assay plates (peristaltic pump) to stop the reaction. Plates were then monitored for fluorescence at 380 nm excitation and 465 nm emission in an Infinite M200 spectrofluorometer (Tecan, San Jose, Calif.).

Solubility Assays.

Compounds were tested for solubility in DMSO and aqueous buffer. Briefly, compounds were dissolved in DMSO at 10 mM and 1 mM. Compounds that appeared soluble by visual inspection were centrifuged at 14000×G for 30 minutes and inspected for pellet formation. Compounds that were soluble in DMSO were further diluted 100-fold into the aqueous assay buffer (200 mM Tris [pH 9.0], 20% glycerol) and vortexed. Compounds that appeared soluble by visual inspection were centrifuged as described above and inspected for pellet formation. Compounds that were not soluble at either 10 mM or 1 mM in DMSO and 100 μM or 10 μM in aqueous assay buffer were not analyzed further.

Steady-State Kinetics of HTS-Identified Inhibitors of DEN2V NS2B-NS3pro.

To determine the mechanism of inhibition and inhibition constants for the compounds, detailed kinetic analyses were performed on compounds identified as protease inhibitors and has been described previously (Tomlinson and Watowich, 2011, Antiviral Res 89:127-35).

West Nile Virus NS2B-NS3pro Expression and Purification.

Plasmid constructs for WNV NS2B-NS3 protease (NS2B-NS3pro) have been previously described (Mueller et al., 2007, Int J Biochem Cell Biol 39:606-14). Expression and purification has been described (Tomlinson and Watowich, 2008, Biochemistry 47:11763-70).

AMC Corrections and Definition of Linear Response of Fluorometer.

To correct for systematic variations in instrument response, AMC dilution series were measured in conjunction with each protease reaction (DEN2V or WNV). These measurements not only defined the linear range and response of the spectrofluorometer, but also allowed for correction at each inhibitor concentration for variation imposed by compound color. Briefly, each concentration of inhibitor as well as a "no inhibitor" control was incubated with five-ten two-fold dilutions of AMC. Relative fluorescence unit data were converted to absolute AMC product concentrations using EXCEL (Microsoft, Redmond, Wash.), where the data were transformed using the slope from the linear regression of the AMC dilution series. Linear regression analysis was performed using GraphPad Prism (GraphPad Software San Diego, Calif.).

Steady-State Kinetics of HTS-Identified Inhibitors of WNV NS2B-NS3pro.

To determine the mechanism of inhibition and inhibition constants for the identified DEN2V lead compounds against WNV NS2B-NS3pro, detailed kinetic analyses were performed using purified WNV NS2B-NS3pro and the fluorophore-linked peptide substrate Boc-GRR-AMC. WNV NS2B-NS3pro kinetic experiments were performed identically to the protocol for DEN2V NS2B-NS3pro kinetics.

Trypsin Activity Validation.

To validate the absence of activity against trypsin, each inhibitor was tested for in vitro trypsin inhibition. Compounds were diluted 100-fold into trypsin cleavage buffer (67 mM sodium phosphate, pH 7.6) for a final concentration of 100 μM and vortexed. Bovine pancreatic trypsin (final concentration 50nM) and BOC-GRR-AMC (final concentration 30 μM) were added to the mixture that was then incubated at room temperature for 30 minutes. Reactions were monitored on a Fluorolog FL3-22 spectrofluorometer (Horiba Jobin Yvon) to quantify fluorescence emitted at 465 nm after excitation at 380 nm. All assays were performed in duplicate.

Example 2

Anthracene-Based Inhibitors of Dengue Virus NS2B-NS3 Protease

Protein expression and purification. The DEN2V NS2B-NS3pro plasmid construct included an ~40 residue central hydrophilic domain from DEN2V NS2B joined to the N-terminal protease domain of the DEN2V NS3 protein by a protease-resistant linker ($Gly_4$-Ser-$Gly_4$) (Li et al., 2005, J Biol Chem 280, 28766-28774). The nucleotide sequence of the plasmid construct was verified by direct sequencing. DEN2V NS2B-NS3pro was expressed and purified to homogeneity as visualized by Coomassie blue staining of proteins separated by SDS polyacrylamide gel electrophoresis (data not shown).

Solubility and Preliminary Inhibition Assays.

Figure 3:
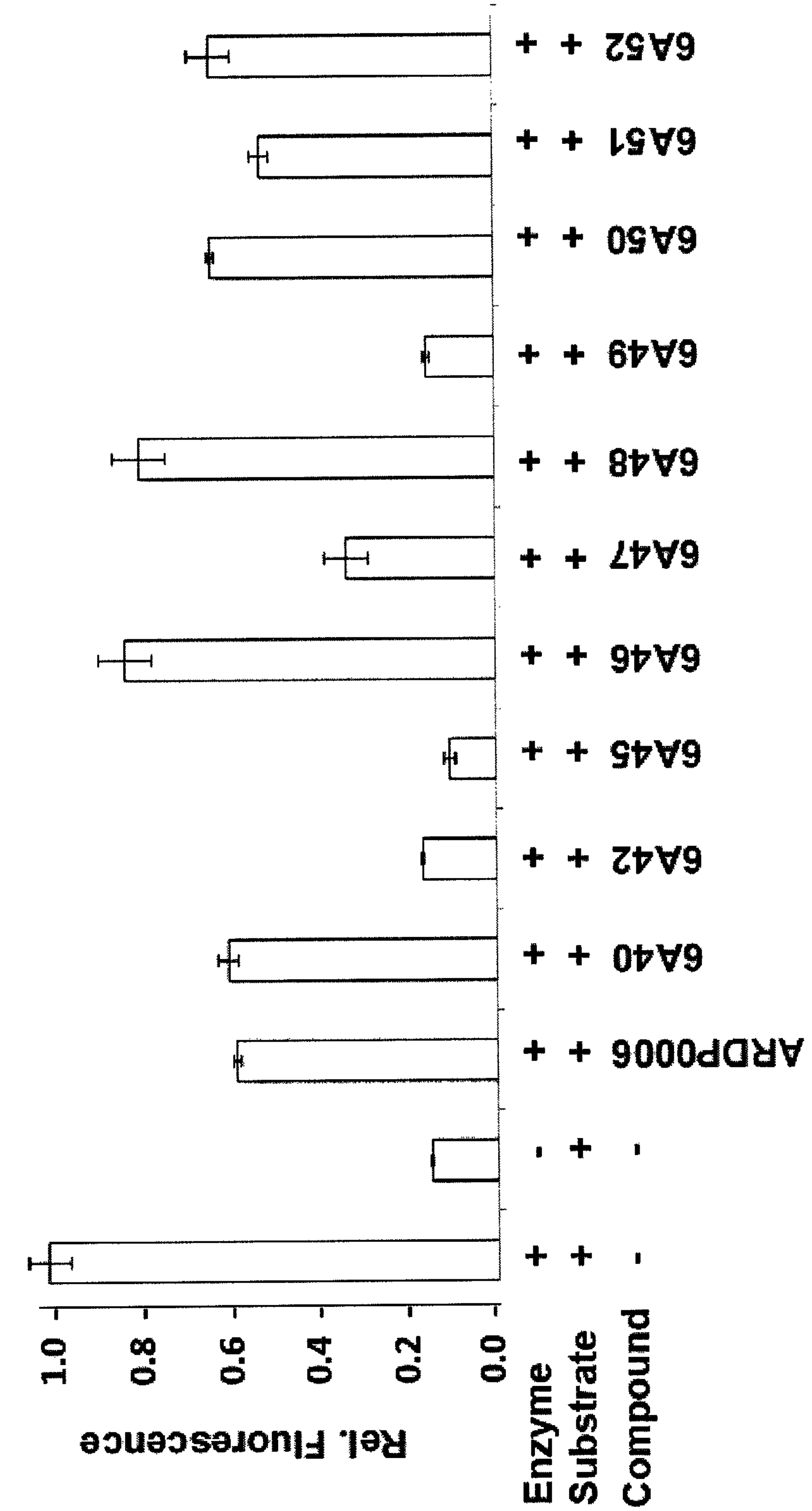
FIG. 3. In vitro NS2B-NS3 protease inhibition assay for soluble analogs of lead inhibitor ARDP0006. Compounds were assayed for in vitro protease inhibition along with "no inhibitor" and no protease controls. Protease activities of each reaction were normalized to the "no inhibitor" controls.

Twenty-three analogs of the previously identified DEN2V protease inhibitor ARDP0006 were purchased for testing against DEN2V NS2B-NS3pro (Table 3). In Table 3, compounds soluble in aqueous buffer were indicated with “S” and insoluble compounds indicated with “NS.” Relative solubilities (clogS, calculated with the OSIRIS program http://www.organic-chemistry.org/prog/peo) were listed in parenthesis. Compound selection was based on commercial availability, computer-predicted aqueous solubility, occurrence of an “anthracene-like” scaffold similar to lead ARDP0006, and distribution of unique functional groups on the scaffold. Only 10 analogs were soluble to at least 10 μM in aqueous assay buffer and 1% DMSO, highlighting the need for more effective computational algorithms to predict compound solubility. The insoluble compounds were removed from further testing. The 10 soluble compounds were tested in a preliminary protease inhibition screen. Four of the 10 compounds demonstrated inhibition significantly better than the parent compound ARDP0006 (FIG. 3), while an additional 4 compounds demonstrated inhibition similar to ARDP0006.

TABLE 3

Analogs of lead compound ARDP0006 that were purchased for testing against DEN2V NS2B-NS3 protease.

| ID | Structure | Solubility (clogS*) |
|---|---|---|
| ARDP0006 | 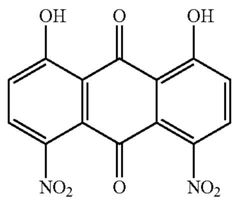 [SMILES: O=C1c2c(O)ccc([N+](=O)[O-])c2C(=O)c2c([N+](=O)[O-])ccc(O)c21] | S (−5.1) |
| 6A24 | 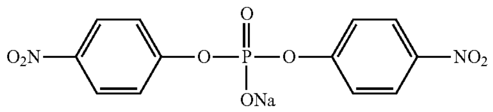 | NS (−4.8) |
| 6A25 | 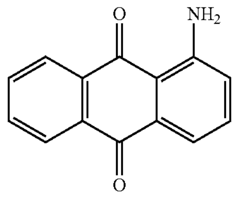 [SMILES: Nc1cccc2c1C(=O)c1ccccc1C2=O] | NS (−4.9) |
| 6A26 | 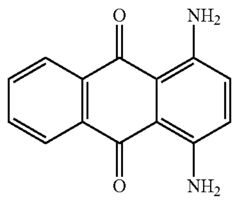 [SMILES: Nc1ccc(N)c2c1C(=O)c1ccccc1C2=O] | NS (−4.9) |

TABLE 3-continued
Analogs of lead compound ARDP0006 that were purchased for testing against DEN2V NS2B-NS3 protease.
| ID | Structure | Solubility (clogS*) |
|---|---|---|
| 6A27 | 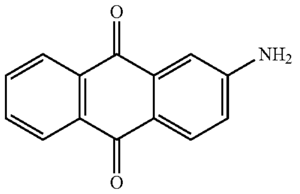 [SMILES: Nc1ccc2c(c1)C(=O)c1ccccc1C2=O] | NS (−4.8) |
| 6A28 | 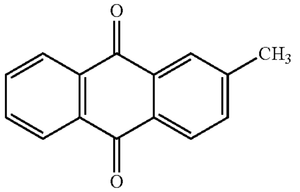 [SMILES: Cc1ccc2c(c1)C(=O)c1ccccc1C2=O] | NS (−5.1) |
| 6A29 | 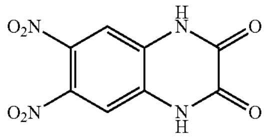 [SMILES: O=c1[nH]c2cc([N+](=O)[O-])c([N+](=O)[O-])cc2[nH]c1=O] | NS (−2.8) |
| 6A30 | 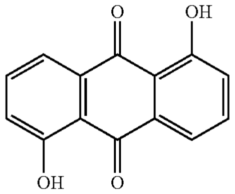 [SMILES: O=C1c2cccc(O)c2C(=O)c2cccc(O)c21] | NS (−4.1) |
| 6A31 | 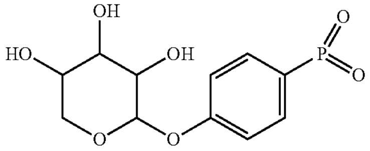 [SMILES: O=P(=O)c1ccc(OC2OCC(O)C(O)C2O)cc1] | NS (−1.8) |
| 6A33 | 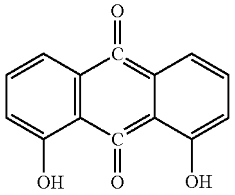 | NS (−4.1) |
| 6A35 | 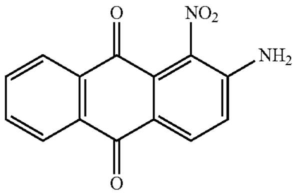 [SMILES: Nc1ccc2c(c1[N+](=O)[O-])C(=O)c1ccccc1C2=O] | NS (−5.3) |

TABLE 3-continued
Analogs of lead compound ARDP0006 that were purchased for testing against DEN2V NS2B-NS3 protease.
| ID | Structure | Solubility (clogS*) |
|---|---|---|
| 6A40 | 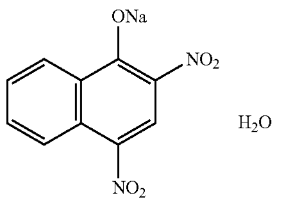 | NS (−3.9) |
| 6A41 | 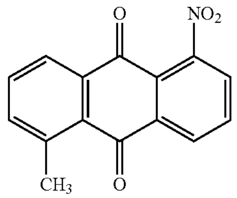 [SMILES: Cc1cccc2c1C(=O)c1cccc([N+](=O)[O-])c1C2=O] | NS (−5.5) |
| 6A42 | 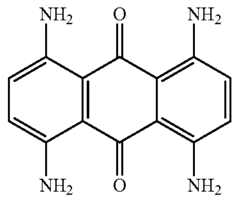 | S (−5.0) |
| 6A44 | 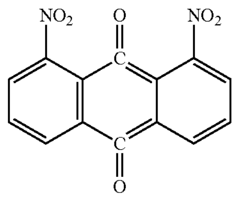 | S (−5.7) |
| 6A45 | 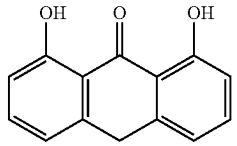 [SMILES: O=C1c2c(O)cccc2Cc2cccc(O)c21] | S (−3.8) |
| 6A46 | 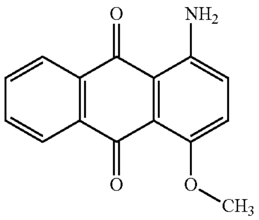 [SMILES: COc1ccc(N)c2c1C(=O)c1ccccc1C2=O] | S (−4.8) |
| 6A47 | 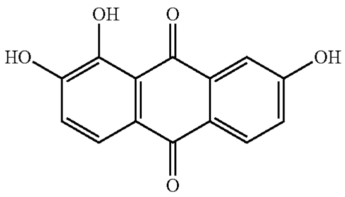 [SMILES: O=C1c2ccc(O)cc2C(=O)c2c1ccc(O)c2O] | S (−3.8) |

TABLE 3-continued

Analogs of lead compound ARDP0006 that were purchased for testing against DEN2V NS2B-NS3 protease.

| ID | Structure | Solubility (clogS*) |
|---|---|---|
| 6A48 | 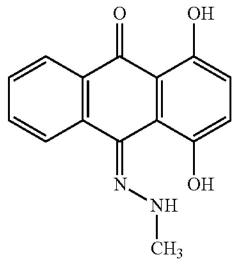 [SMILES: CN/N=C1/c2ccccc2C(=O)c2c(O)ccc(O)c21] | S (−4.5) |
| 6A49 | 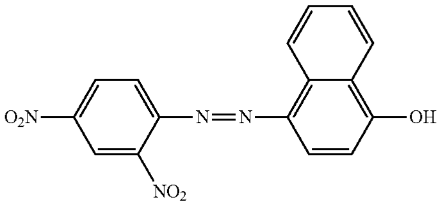 | S (−6.4) |
| 6A50 | 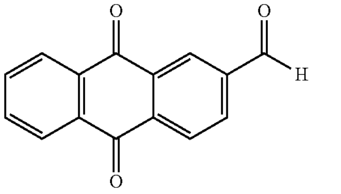 [SMILES: O=Cc1ccc2c(c1)C(=O)c1ccccc1C2=O] | S (−5.1) |
| 6A51 | 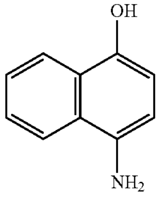 [SMILES: Nc1ccc(O)c2ccccc12] | S (−3.0 |
| 6A52 | 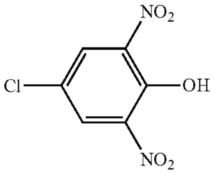 [SMILES: O=[N+]([O-])c1cc(Cl)cc([N+](=O)[O-])c1O] | S (−3.0) |
| 6A53 | 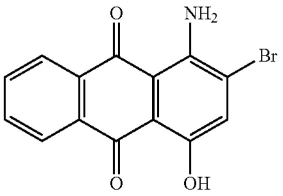 [SMILES: Nc1c(Br)cc(O)c2c1C(=O)c1ccccc1C2=O] | NS (−5.3) |

*calculated log of the compound's aqueous solubility (S), with units for S being mol $l^{-1}$ Kinetics of Inhibitors of DEN2V NS2B-NS3pro.

Detailed kinetic analyses were completed on analogs 6A42, 6A45, 6A47, and 6A49 to determine their kinetic parameters, inhibition constants, and mechanism of inhibition. These compounds showed significant inhibition of DEN2V NS2B-NS3pro in the preliminary inhibition assay. Several inhibition mechanisms, including competitive, uncompetitive, and mixed noncompetitive, were examined for each compound. Analyses were performed using Dynafit and kinetic parameters for each model were optimized to provide the best global fit to the experimental data. Final model selection was based on fitting accuracy, parameter errors, and model discrimination analysis within the Dynafit program (Kuzmic, 2009, Methods Enzymol 467, 247-280).

Figure 4:
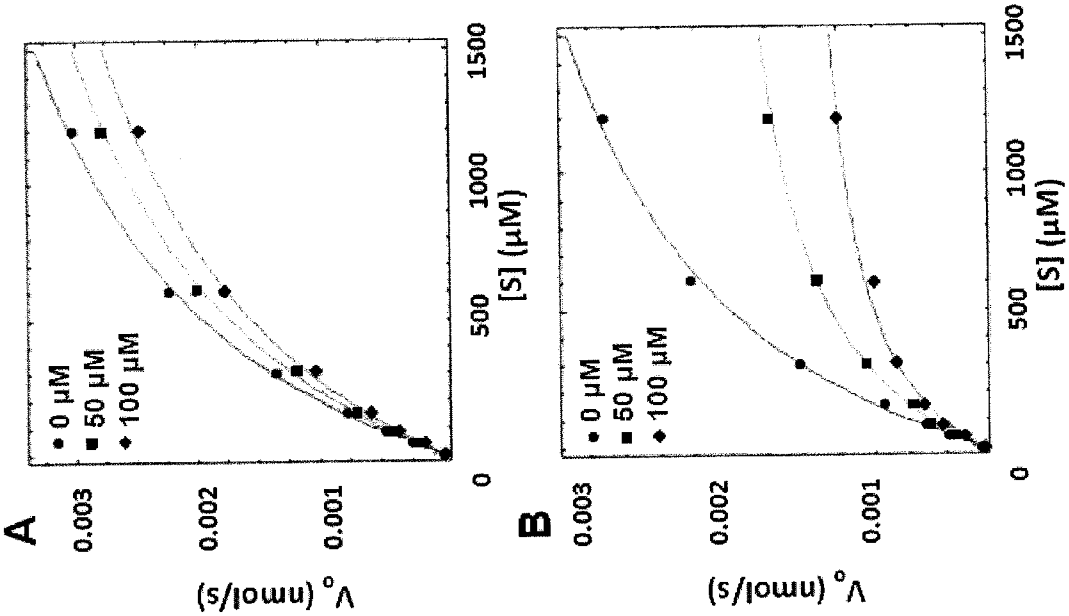
FIGS. 4A-4B. DEN2V NS2B-NS3 protease inhibition curves for lead inhibitor ARDP0006 (A) and analog 6A42 (B). Concentrations of inhibitor tested were 0 (circles), 50 (squares), and 100 (diamonds) μM. Data were analyzed with the program Dynafit according to Scheme 1.

Analysis of kinetic data clearly showed that ARDP0006 and analogs 6A42, 6A45, 6A47, and 6A49 inhibited DEN2V NS2B-NS3pro in this assay (Table 2). The selected inhibition models with computed model parameters (Table 4) had excellent fits to the experimental data as shown by representative curves for the parent compound ARDP0006 (FIG. 4A) and analog 6A42 (FIG. 4B). A competitive inhibition model best described the ARDP0006 kinetic inhibition data. In contrast, mixed noncompetitive inhibition models (Scheme 1) best described the kinetic inhibition data for analogs 6A42, 6A45, 6A47, and 6A49.

TABLE 4

Inhibition constants for analogs with in vitro activity against DEN2V NS2B-NS3pro.

| Compound | $K_i1$ (μM) | $K_i2$ (μM) | Mechanism |
|---|---|---|---|
| ARDP0006 | 432 ± 46 | — | Competitive |
| 6A42 | 158 ± 32 | 43 ± 3 | Mixed |
| 6A45 | 47 ± 15 | 77 ± 35 | Mixed |
| 6A47 | 215 ± 119 | 20 ± 2 | Mixed |
| 6A49 | 15 ± 3 | 10 ± 1 | Mixed |

Control experiments were performed with substrate concentrations ranging from 0 to 5 mM to allow unequivocal determination of $V_{max}$ and thus obtain highly accurate kinetic parameters. It should be noted that similar to findings for WNV NS2B-NS3pro (Tomlinson and Watowich, 2008, Biochemistry 47, 11763-11770), DEN2V NS2B-NS3pro demonstrated substrate inhibition though at high ([S]=5 mM) substrate concentrations. Kinetic analysis performed with different ranges of substrate concentrations produced similar kinetic parameters, although the calculated error estimates were slightly smaller for experiments performed with the largest range of substrate concentrations ([S] varied from 0 to 5 mM). For this reason, $K_m$ and $k_{cat}$ were constrained to the values obtained from the higher substrate experiments for all analyses. The kinetic parameters were essentially the same for all kinetic assays with $K_m$=673±49 μM and $k_{cat}$=0.02±0.002 $s^{-1}$ Trypsin Inhibition.

To determine if the inhibitors were selective for DEN2V NS2B-NS3pro, each compound was tested for its ability to inhibit trypsin cleavage of the chromogenic substrate N-α-benzoyl-DL-arginine 4-nitroanilide hydrochloride (BAPNA) and the fluorogenic substrate BOC-GRR-AMC. Detailed analysis of trypsin cleavage of the fluorogenic substrate with DEN2V NS2B-NS3pro inhibitors showed that 6A49 did not inhibit trypsin, 6A42 and 6A47 were mixed noncompetitive trypsin inhibitors, ARDP0006 was an uncompetitive trypsin inhibitor, and 6A45 and benzamidine were competitive trypsin inhibitors (Table 5). Analysis of the trypsin reactions were highly reproducible, with kinetic parameters calculated as $K_d$=34±2 μM and $k_{cat}$=0.06±0.005 $s^{-1}$. Compounds that had a $K_i1$ value for the fluorogenic substrate (either competitive or mixed noncompetitive inhibition mechanisms) also inhibited trypsin cleavage of the chromogenic substrate, with the two competitive inhibitors showing the strongest degree of inhibition (data not shown). This was noteworthy, as we have observed compounds (e.g., ARDP0006 and inhibitors from unrelated high-throughput screening studies) that inhibited trypsin cleavage of the fluorogenic substrate but not the chromogenic substrate. In these cases, kinetic studies with the fluorogenic substrate revealed an uncompetitive inhibition mechanism ($K_i2$ only), which implied interactions between the inhibitor (I) and enzyme-substrate (ES) complex, but not the apo-enzyme (see Scheme 1).

Scheme 1.

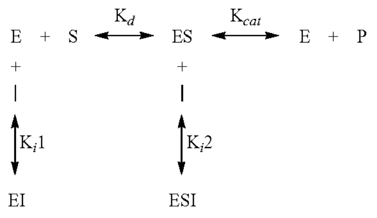

TABLE 5

Trypsin inhibition constants from kinetic studies.

| Compound | $K_i1$ trypsin (μM) | $K_i2$ trypsin (μM) | Mechanism |
|---|---|---|---|
| ARDP0006 | — | 13 ± 0.1 | Uncompetitive |
| 6A42 | 60 ± 13 | 167 ± 20 | Mixed |
| 6A45 | 0.6 ± 0.07 | — | Competitive |
| 6A47 | 4 ± 0.7 | 25 ± 3 | Mixed |
| 6A49 | — | — | No inhibition |
| Benzamidine | 21.6 ± 1 | — | Competitive |

Compound 6A49 inhibited the DEN2V NS2B-NS3 protease but not trypsin. In contrast, compounds 6A42, 6A45, and 6A47 inhibited both the DEN2V NS2B-NS3 protease and trypsin, and thus may not be good candidates for further optimization. However, these compounds provide useful information to understand determinants of binding affinity.

Combined Modeling and SAR of the Inhibitor-Protease Complex.

Figure 5:
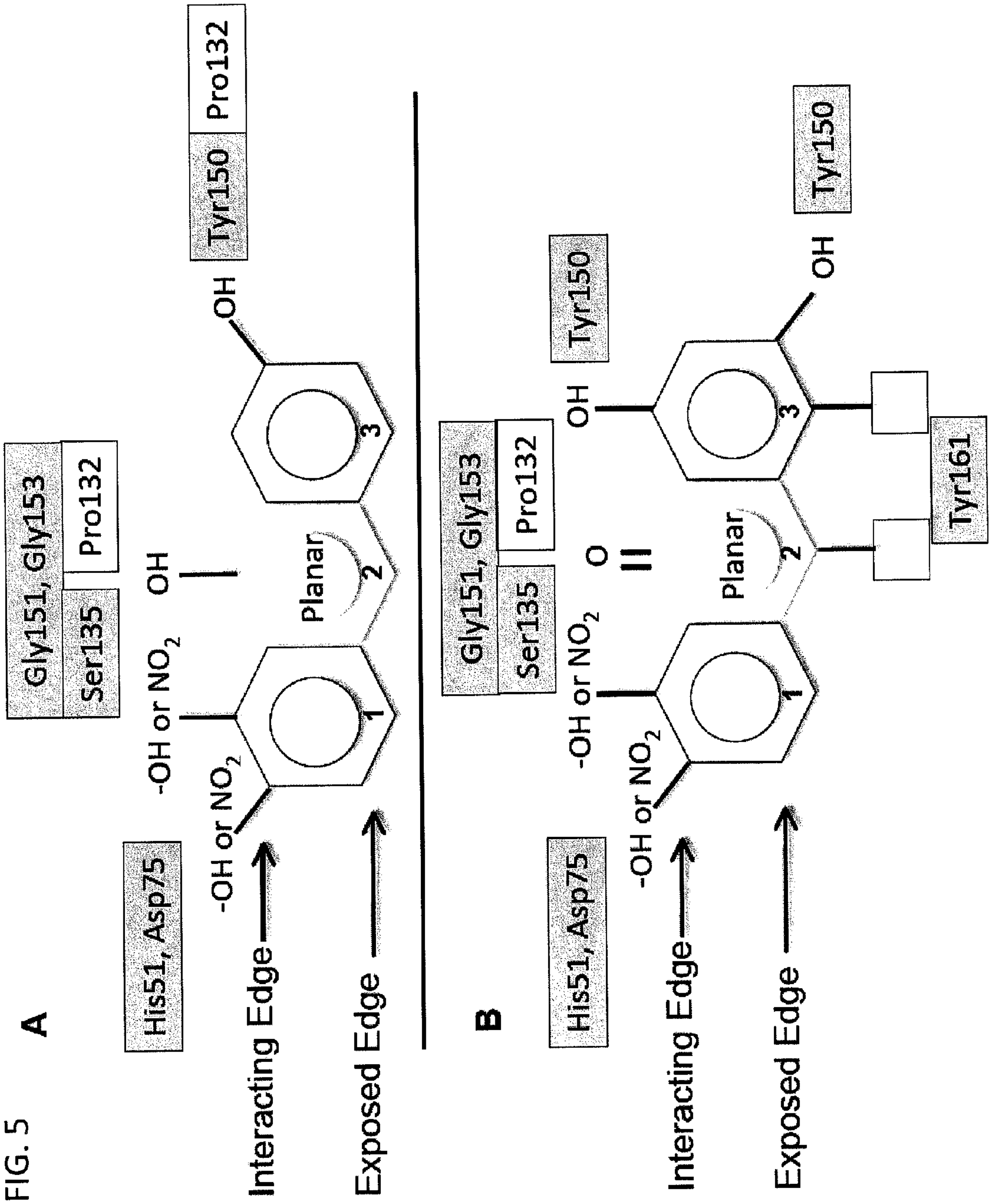
FIGS. 5A-5B. SAR suggested favorable (A) and unfavorable (B) arrangements of functional groups around the anthracene-based scaffold. Boxes represent protease residues predicted to interact with inhibitor pharmacophores based on the described computational docking studies. Grey shaded boxes represent residues that were invariant among dengue, West Nile, and Japanese encephalitis viruses.

The program AutoDock Vina (Trott and Olson, 2010, J Comput Chem 31, 455-461) was used to initially position the DEN2V NS2B-NS3pro inhibitors ARDP0006, 6A42, 6A45, 6A47, and 6A49 into the DEN2V apo-enzyme (PDB identifier 2FOM; (Erbel et al., 2006, Nat Struct Mol Biol 13, 372-373) active site to predict likely intermolecular interactions. For each inhibitor, the AutoDock Vina program predicted several similar bound conformations that had energy differences of <1 kcal $mol^{-1}$. Upon examination and comparison of the top scored conformations for all ligands, it was apparent that there was a prevailing low energy conformation that was similar for all inhibitors. In this conformation, interactions were between catalytic or P1 pocket residues of the active site and functional groups on only one edge of the inhibitors. Significant interactions occurred between hydroxyl and nitro groups of the inhibitors and conserved residues that constituted the catalytic triad (His51, Asp75, Ser135) and P1 pocket (Gly151, Gly153, Tyr150) of the protease. Inhibitors 6A42 and 6A47 shared the anthraquinone scaffold of the parent compound. ARDP0006; these three compounds all "docked" such that the central ring's carbonyl oxygen on the inhibitor's "interacting edge" contacted the hydroxyl group of Ser135 (FIG. 5). The hydroxyl groups attached to the flanking rings of the anthraquinones were predicted to interact with the imidazole ring of His51 and P1 pocket residues Tyr150, Gly151, and Gly153. Compound 6A45 had a similar scaffold but with functional groups along only one edge (termed the "interacting edge"), and demonstrated better inhibitory activity than ARDP0006, 6A42, and 6A47. Key interactions were between the hydroxyl groups of 6A45 and the imidazole ring of His51 and the hydroxyl group of Tyr150. The 6A49 inhibitor did not have the anthracene triplet ring structure, but had a comparable extended planar structure formed from the two aromatic rings connected by an azo linkage. This inhibitor had the lowest $K_i1$ (i.e., tightest binding) of the initial set of analogs tested, and was the only inhibitor that formed an additional contact between a nitro group of the inhibitor and the carboxyl group of Asp75. Finally, the docked structures of ARDP0006, 6A42, and 6A47 had functional groups on the "exposed edge" of the anthracene scaffold that interacted with Tyr161 (FIG. 5). Since these compounds exhibited relatively high $K_i1$ values (i.e., low activity), these interactions likely contributed to reduced inhibitor binding.

This structure-based analysis suggested an improved inhibitor design (at least within the constraints of the compounds analyzed) for DEN2V NS2B-NS3pro (Table 6). In Table 6, Compounds soluble in aqueous buffer were indicated with "S" and insoluble compounds indicated with "NS." Relative solubilities (clogS, calculated with the OSIRIS program) were listed in parenthesis.

flaviviruses, interactions between them and an inhibitor would be preferred to minimize drug resistance. An additional interaction occurred with Pro132 that was located adjacent to Ser135. Interaction with Pro132 may interfere with its interactions with Ser135. Hydroxyl or carbonyl groups on the interacting edge of the central ring were predicted to interact with similar protease residues, although the latter group correlated with decreased activity perhaps because of increased bond distances. Finally, functional groups on the exposed edge of the scaffold that interacted with Tyr161 should be removed since they correlated with decreased inhibitor binding.

To test the qualitative predictive power of the SAR, 4 "second series" anthracene-based analogs (6A60, 6A61, 6A62, 6A63) were purchased for testing (Table 4). Compound 6A60 was predicted to show better activity relative to the initial set of analogs as it contained functional groups in locations that correlated with improved activity. Compound 6A61 was predicted to have intermediate activity since it had

TABLE 4

"Second series" analogs used for SAR validation. Inhibition parameters were determined from kinetic studies with DEN2V NS2B-NS3 and trypsin proteases.

| | | | DEN2V NS2B-NS3 | | | Trypsin | | |
|---|---|---|---|---|---|---|---|---|
| Compound | Structure | Solubility (clogS*) | $K_i1$ (μM) | $K_i2$ (μM) | Mechanism | $K_i1$ (μM) | $K_i2$ (μM) | Mechanism |
| 6A60 | 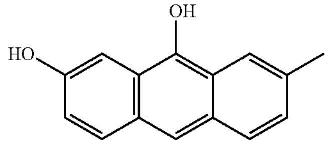 [SMILES: Cc1ccc2cc3ccc(O)cc3c(O)c2c1] | S (−3.9) | 7 ± 5 | 3 ± 1 | Mixed | — | — | No inhibition |
| 6A61 | 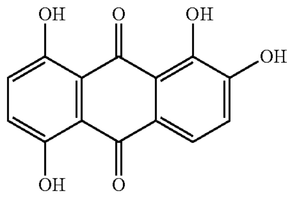 [SMILES: O=C1c2ccc(O)c(O)c2C(=O)c2c(O)ccc(O)c21] | S (−3.6) | 72 ± 15 | 10 ± 2 | Mixed | — | — | No inhibition |
| 6A62 | 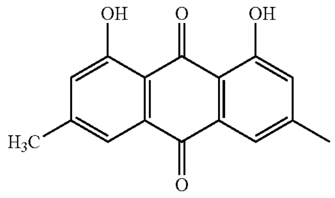 | S (−4.2) | 508 ± 47 | — | Competitive | — | 5 ± 0.4 | Uncompetitive |
| 6A63 | 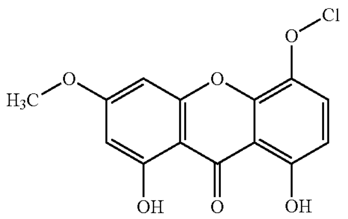 [SMILES: COc1cc(O)c2c(=O)c3c(O)ccc(OCl)c3oc2c1] | NS (−4.4) | | | | | | |

*calculated log of the compound's aqueous solubility (S), with units for S being mol $l^{-1}$ The inhibitors' core was an anthracene (or extended planar) scaffold and stabilizing H-bonding interactions occurred between functional groups located on the interacting edge of the inhibitor and catalytic (His51, Asp75, Ser135) and P1 pocket (Gly151, Gly153, Tyr150) residues of the protease. Since these protease residues were highly conserved among key functional groups on the interacting edge, but additional functional groups on the exposed edge of rings 1 and 2. Compound 6A62 was predicted to be a relatively poor inhibitor due to the presence of functional groups on the exposed edge of each ring of the anthracene scaffold. Similar to 6A62, compound 6A63 was also predicted to be a relatively poor binder. Unfortunately, 6A63 was not soluble in the kinetic reaction buffer and was not tested further. Kinetic assays to determine inhibition constants for the three soluble analogs validated our predictions (Table 4), with 6A60 found to have the lowest $K_i1$ of all anthracene-based analogs. Moreover, this small molecule was a specific protease inhibitor since it did not inhibit trypsin cleavage activity (Table 4).

Figure 6:
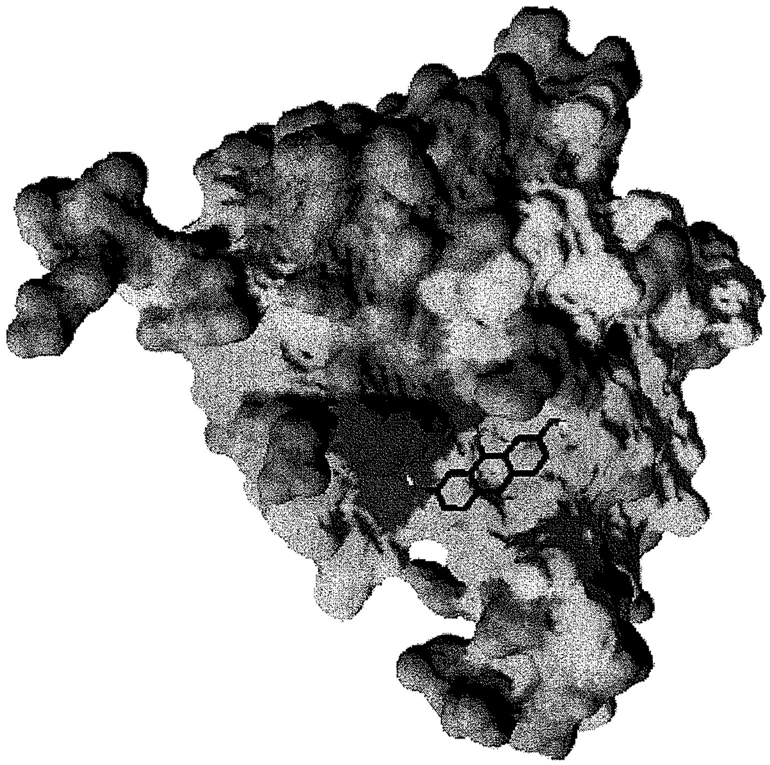
FIG. 6. Predicted interaction of compound 6A60 with DEN2V NS2B-NS3. Compound 6A60 was docked into the active site of the dengue protease using Vina docking software. Conserved residues were colored green, the conserved catalytic residues were colored red, and other (nonconserved) protease residues were colored blue.

Compound 6A60 was predicted to bind to the DEN2V NS2B-NS3 active site such that functional groups on the interacting edge of the anthracene made contacts with residues that were conserved among flavivirus proteases (FIG. 6). Favorable contacts were predicted between the hydroxyl of ring 1 and the NH of the side-chain of catalytic residue His51 (2.3 Å) and the carboxyl group of the catalytic residue Asp75 (2.8 Å), between the central hydroxyl of 6A60 and the hydroxyl groups of catalytic residue Ser135 (2.4 Å) and the P1 pocket residue Tyr150 (3.3 Å), and between the hydroxyl of ring 3 and the hydroxyl groups of catalytic residue Ser135 (2.4 Å) and P1 pocket residue Tyr150 (3.3 Å). Compound 6A61 demonstrated the next lowest $K_i1$ value and was predicted to interact with Ser135, Tyr150, and Tyr160. This compound also did not inhibit trypsin.

A combined SAR and docking analysis using all tested anthracene-based analogs suggested that the inhibitors (with the exception of ARDP0006) formed contacts with the catalytic residue His51 of the protease. In addition, predicted interactions with Tyr150 correlated with improved (i.e., lower) $K_i1$ values. Inhibitors that were predicted to favorably interact with the side-chain of catalytic residue Asp75 (i.e., 6A49 and 6A60) were observed to have the lowest $K_i1$ values. The weak activity of 6A62 provided additional support that functional groups on the exposed edge of ring 3 (positioned to interact with Tyr161) compromised inhibitor binding. Finally, interactions with the side-chain of catalytic residue Asp75 (as predicted for 6A60 and 6A49) correlated with improved activity.

Materials and Methods

Analogs.

Pubchem and Sigma Aldrich structure similarity search programs were employed to identify commercially-available analogs of the ARDP0006 lead (Tomlinson et al., 2009, Antiviral Res 82, 110-114). The OSIRIS property explorer (world wide web through organic-chemistry.org) was used to determine clogP and predicted solubility, and compounds with predicted solubility significantly less than ARDP0006 were not selected for testing. Analogs were purchased from Sigma Aldrich (St. Louis, Mo.) and Chembridge Corporation (San Diego, Calif.).

Solubility Assays.

Compounds were tested for solubility in DMSO and aqueous buffer according to the previously described protocol (Tomlinson et al, 2009, Antiviral Res 82, 110-114). Briefly, compounds were dissolved in DMSO at 10 mM and 1 mM. Compounds that appeared soluble by visual inspection were centrifuged at 11,000×g (Spectrafuge 16M, LabNet International, Edison, N.J.) for 30 min and inspected for insoluble pellet formation. Compounds soluble in DMSO were diluted 100-fold into aqueous assay buffer (200 mM Tris [pH 9.0], 20% glycerol) and vortexed. Compounds that appeared soluble in aqueous buffer by visual inspection were centrifuged as described above and inspected for pellet formation. Compounds that precipitated at concentrations of 1 mM in DMSO or 10 μM in aqueous assay buffer were removed from further study.

Expression and Purification of DEN2V NS2B-NS3pro.

The expression and purification of DEN2V (strain TSV01; Genbank accession number AY037116) NS2B cofactor linked to the protease domain of NS3 (NS2B-NS3pro); plasmid a generous gift from Dr. Lim Siew Pheng of the Novartis Institute for Tropical Diseases, Singapore) was modified from previously described protocols (Li et al., 2005, J Biol Chem 280, 28766-28774). Briefly, expression was identical to that previously described with the exception that cultures were grown at 25° C. for 8 hrs after IPTG induction. For purification, pelleted cells were first resuspended in chilled lysis buffer (50 mM HEPES [pH 7.5], 300 mM NaCl, 5% glycerol). Cell lysis was facilitated by the addition of DNase (30 μm/ml), $MgCl_2$ (10 mM), lysozyme (300 μg/ml), and Triton X-100 (final concentration 0.5% v/v). The lysis mixture was incubated on ice, rocked gently for 1 hr, and centrifuged at 4° C. and ~12,500×g for 30 min. The soluble fraction was applied to a nickel affinity column formed from nickel sephadex beads (Amersham Biosciences) pre-equilibrated with lysis buffer. The beads were washed with lysis buffer and increasing concentrations of imidazole (5 mM, 10 mM, and 20 mM, in lysis buffer) to remove contaminating proteins. Bound NS2B-NS3pro was eluted from the column with lysis buffer and 150 mM imidazole in 1 ml aliquots, dialyzed into storage buffer (50 mM Tris [pH 7.5], 300 mM NaCl), portioned into 1 ml aliquots with 25% glycerol, flash-frozen in liquid nitrogen, and stored at −80° C. Protein concentration was determined by UV spectroscopy.

Preliminary Inhibition Assays.

Protease activity experiments were performed in vitro using purified DEN2V NS2B-NS3pro and the 7-amino-4-methylcoumarin (AMC) fluorophore-linked peptide substrate Boc-GRR-AMC (Bachem, USA). Preliminary activity experiments were performed by incubating each soluble compound with 100 nM DEN2V NS2B-NS3pro and 100 μM Boc-GRR-AMC (Bachem, USA) in cleavage buffer (200 mM Tris [pH 9.5], 20% glycerol) for 30 min at 25° C. Release of free AMC was monitored using a Fluorolog FL3-22 spectrofluorometer (Horiba Jobin Yvon) to record fluorescence emitted at 465 nm following excitation at 380 nm. Assays were performed in duplicate. Protease reactions performed with 100 μM aprotinin, a known broad-spectrum serine protease inhibitor, showed fluorescence levels that were similar to that of the "substrate alone" background control (data not shown).

Steady-State Kinetics of Inhibitors of DEN2V NS2B-NS3pro.

Detailed kinetic studies were performed under similar reaction conditions as described above using a broad range of substrate concentrations. Reaction progress was monitored by release of free AMC every five minutes for at least 30 minutes. All assays were performed at least two times in duplicate.

To correct for potential variations in instrument response, fluorescence from an AMC dilution series was recorded in conjunction with each protease reaction. These measurements defined the linear range and response of the spectrofluorometer, and established an AMC standard curve to correct for concentration-dependent absorption changes due to colored compounds. Briefly, each concentration of tested analog and a "no inhibitor" control were incubated with a two-fold dilution series of AMC. Relative fluorescence unit data were converted to absolute AMC product concentrations using EXCEL (Microsoft, Redmond, Wash.), where the data were transformed using the slope from the linear regression of the AMC dilution series. Linear regression analysis was performed using GraphPad Prism (GraphPad Software San Diego, Calif.).

For each tested analog, the mechanism of inhibition and inhibition constant(s) were determined from rigorous kinetic assays. Three concentrations of each inhibitor were separately mixed with cleavage buffer and DEN2V NS2B-NS3pro (100 nM final concentration). Kinetic assays were performed in duplicate in 96-well black plates (100 ul final volume/well). Serial dilutions of substrate were added to the wells for final substrate concentrations of 37.5 μM, 75 μM, 150 μM, 300 μM, 600 μM, and 1200 μM. Fluorescence of released AMC was monitored every 5 min for 30 min by emission at 465 nm (excitation 380 nm). To convert relative fluorescence units to absolute AMC concentrations, an AMC dilution series was performed as described above. Linear regression analysis was performed using GraphPad Prism (GraphPad Software San Diego, Calif.) to determine initial velocities for each reaction from AMC product concentrations and reaction times. Errors associated with each initial velocity measurement were consistently <2%.

Trypsin Inhibition Assays.

Bovine pancreatic trypsin (Sigma Aldrich, St. Louis) and N-α-Benzoyl-DL-arginine 4-nitroanilide hydrochloride (BAPNA) substrate (Sigma Aldrich, St. Louis) were used for trypsin inhibition assays. Trypsin stock solutions were prepared in sodium phosphate buffer (67 mM [pH 7.6]). Trypsin (60 μM) was incubated with chromogenic BAPNA (500 μM) and release of the para-nitroanilide product monitored using a DU640 spectrophotometer (Beckman Coulter, USA) to measure absorption at 415 nm. The slope of the progress curve was determined using linear regression and used as a baseline for comparison with inhibitor reactions. Each analog was tested at 100 μM final concentration for inhibition of trypsin. Benzamidine (Sigma Aldrich, St. Louis), a well-documented inhibitor of trypsin (Markwardt et al., 1968, Eur J Biochem 6, 502-506), was used as a trypsin inhibitor control.

Steady-State Kinetics of Inhibitors of Trypsin.

Detailed kinetic experiments were completed for analogs that inhibited trypsin in assays with the chromogenic BAPNA substrate. Experiments used the BOC-GRR-AMC substrate and were performed as described above with a 50 nM final concentration of trypsin. The fluorescence of AMC released in the trypsin assays was monitored every three minutes for twenty-four minutes.

Kinetic Analysis.

Initial reaction velocity versus substrate concentration data were analyzed with Dynafit (Biokin, Watertown, Mass.) (Kuzmic, 1996, Anal Biochem 237, 260-273) to determine the kinetic parameters, reaction mechanism, and inhibition model. Models tested included competitive, uncompetitive, and mixed noncompetitive inhibition, with and without substrate inhibition. Inhibition data were analyzed using global non-linear least square fitting.

Modeling and Structure Activity Relationship (SAR).

The AutoDock Vina program (Trott and Olson, 2010, J Comput Chem 31, 455-461) was used to computationally bind each small molecule inhibitor to DEN2V NS2B-NS3pro (PDB identifier 2FOM; (Erbel et al., 2006, Nat Struct Mol Biol 13, 372-373). The inhibitor conformation with the lowest docking score was assumed to represent the inhibitor/protease structure and the intermolecular interactions analyzed in detail using Swiss-PDBViewer (Guex and Peitsch, 1997, Electrophoresis 18, 2714-2723). Protease residues that interacted with inhibitor functional groups were tabulated if the interacting atoms were within 4 Å of each other. These interactions were used to develop a preliminary SAR (Patani and LaVoie, 1996, Chem Rev 96, 3147-3176) for this system.

The invention claimed is:

1. An inhibitor of dengue and/or West Nile viral protease having a general formula of Formula I:

Formula I

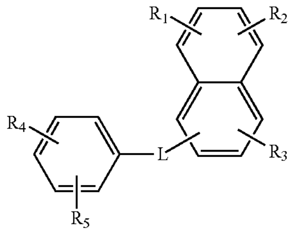

where $R_1$, $R_2$, $R_3$, $R_4$, and $R_5$ are independently hydrogen, hydroxyl, nitro, amine, or $C_1$-$C_4$ alkyl, wherein at least one of $R_4$ and $R_5$ is hydroxyl, nitro, or amine, or form a heterocycle; and L is —C═N—, —N═N—, or —C(O)NH—.

2. A method of preventing or treating flavivirus infection in a subject comprising administering a therapeutically effective amount of an inhibitor of claim 1, wherein the flavivirus infection is a dengue virus infection or a West Nile virus infection.

3. The inhibitor of claim 1, wherein $R_1$ is hydrogen, and $R_2$ and $R_3$ are hydroxyl.

4. The inhibitor of claim 3, where $R_2$ is at the 3 position and $R_3$ is at the 6 position.

5. The inhibitor of claim 4, wherein $R_4$ and $R_5$ form a 1,3-dioxolane.

6. The inhibitor of claim 5, wherein L is —N═N—.

7. The inhibitor of claim 6, wherein L is at the beta position of the naphthalene moiety.

8. The inhibitor of claim 1 having a structural formula of

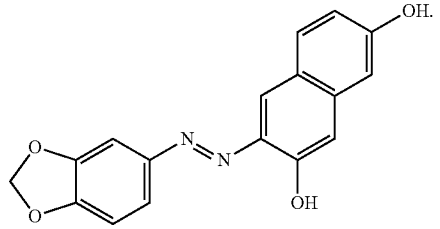 [SMILES: Oc1ccc2cc(/N=N/c3ccc4c(c3)OCO4)c(O)cc2c1]

9. The inhibitor of claim 1, wherein $R_4$ and $R_5$ are independently hydroxyl, nitro, amine, or $C_1$-$C_4$ alkyl.

10. The inhibitor of claim 1, wherein $R_4$ and $R_5$ are joined to form a heterocycle.

11. The inhibitor of claim 10, wherein the heterocycle is 1,3-dioxolane.

12. The inhibitor of claim 1, wherein L is —C(O)NH—.

* * * * *